US012727839B2

(12) United States Patent
Lee et al.

(10) Patent No.: US 12,727,839 B2
(45) Date of Patent: Sep. 8, 2026

(54) IMAGE RECONSTRUCTION INCORPORATING MAXWELL FIELDS AND GRADIENT IMPULSE RESPONSE FUNCTION DISTORTION

(71) Applicant: UNIVERSITY OF SOUTHERN CALIFORNIA, Los Angeles, CA (US)

(72) Inventors: Nam Gyun Lee, Los Angeles, CA (US); Krishna Shrinivas Nayak, Long Beach, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 375 days.

(21) Appl. No.: 18/284,010

(22) PCT Filed: Apr. 1, 2022

(86) PCT No.: PCT/US2022/023153

§ 371 (c)(1),
(2) Date: Sep. 25, 2023

(87) PCT Pub. No.: WO2022/212907

PCT Pub. Date: Oct. 6, 2022

(65) Prior Publication Data

US 2024/0164737 A1 May 23, 2024

Related U.S. Application Data

(60) Provisional application No. 63/170,096, filed on Apr. 2, 2021.

(51) Int. Cl.

*A61B 6/00* (2024.01)
*A61B 5/055* (2006.01)

(Continued)

(52) U.S. Cl.

CPC ............ *A61B 6/5258* (2013.01); *A61B 5/055* (2013.01); *G06T 12/30* (2026.01); *G16H 30/40* (2018.01)

(58) Field of Classification Search

CPC ......... A61B 5/055; A61B 6/5258; A61B 5/05; G06T 2207/10088; G06T 11/008;

(Continued)

(56) References Cited

U.S. PATENT DOCUMENTS 8,094,907 B1 1/2012 Meyer et al.
8,384,383 B2 * 2/2013 Frahm ................ G01R 33/4824 324/309

(Continued)

FOREIGN PATENT DOCUMENTS

WO WO 2010-082193 7/2010

OTHER PUBLICATIONS

Vannesjo, Signe J., et al. "Gradient system characterization by impulse response measurements with a dynamic field camera." Magnetic resonance in medicine 69.2 (2013): 583-593. (Year: 2013).*

(Continued)

*Primary Examiner* — Courtney Joan Nelson
(74) *Attorney, Agent, or Firm* — Snell & Wilmer LLP

(57) ABSTRACT

A system, computer readable medium, apparatus and/or method for magnetic resonance imaging (MRI) reconstruction that mitigates local blurring caused by static off-resonance and concomitant fields. The MRI reconstruction system may use phantom-based gradient impulse response function (GIRF) measurements and analytic expressions to predict the concomitant fields. GIRFs capture gradient delays, eddy current effects, and mechanically induced field oscillations. For each gradient axis, a MR system is perturbed with a set of input gradients. Gradients predicted with (Continued)

phantom-based GIRFs can better estimate concomitant fields than nominal gradients. A novel image reconstruction method incorporates higher-order Maxwell fields and GIRF trajectory corrections and may be treated as "invisible" field probes that require no special hardware but GIRFs measured with phantom-based methods and an analytic model of concomitant fields that depends on coil geometry and severity of gradient non-linearity.

8 Claims, 10 Drawing Sheets

(51) Int. Cl.
*G06T 12/30* (2026.01)
*G16H 30/40* (2018.01)

(58) Field of Classification Search
CPC ......... G06T 7/0012; G06T 7/269; G06T 7/70; G16H 30/40; G16H 50/20
See application file for complete search history.

(56) References Cited

U.S. PATENT DOCUMENTS

| | | | | |
|---|---|---|---|---|
| 10,353,039 | B2 * | 7/2019 | Constable ............ | G01R 33/561 |
| 2012/0008842 | A1 | 1/2012 | Hinks et al. | |
| 2018/0203088 | A1 | 7/2018 | Tao et al. | |
| 2020/0402211 | A1 | 12/2020 | Wang et al. | |

OTHER PUBLICATIONS

International Search Report and Written Opinion for International PCT Patent Application No. PCT/US2022/023153, Jul. 25, 2022, 11 pages.

Nam G Lee et al: "MaxGIRF: Image Reconstruction Incorporating Maxwell Fields and Gradient Impulse Response Function Distortion", Proceedings of The 2021 ISMRM & Smrt Annual Meeting & Exhibition, May 15-20, 2021, ISMRM, 2030 Addison Street, 7TH Floor, Berkeley, CA 94704 USA, No. 624, Apr. 30, 2021 (Apr. 30, 2021).

Testud Frederik et al: "Single-shot imaging with higher-dimensional encoding using magnetic field monitoring and concomitant field correction : Single-Shot Higher-Dimensional Imaging", Magnetic Resonance in Medicine, vol. 73, No. 3, Mar. 31, 2014 (Mar. 31, 2014).

S. Johanna Vannesjo et al: "Image reconstruction using a gradient impulse response model for trajectory prediction", Magnetic Resonance in Medicine, vol. 76, No. 1, Jul. 1, 2016 (Jul. 1, 2016), pp. 45-58.

King K F et al: "Concomitant gradient field effects in spiral scans", Magnetic Resonance in Medicine, Wiley-Liss, US, vol. 41, No. 1, Jan. 1, 1999 (Jan. 1, 1999), pp. 103-112.

Hui Liu et al: "Accurate Measurement of Magnetic Resonance Imaging Gradient Characteristics", Materials, vol. 7, No. 1, Dec. 19, 2013 (Dec. 19, 2013), pp. 1-15.

Extended European Search Report, EP Applic. No. 22782333.3, European Patent Office, Nov. 27, 2024, 10 pages.

* cited by examiner

603

Off-isocenter dependence of concomitant fields at 0.55T

No conc. fields
z = 50 mm
z = 100 mm
z = 150 mm
z = 200 mm

NUFFT
8.68%
23.37%
30.88%
34.78%
37.26%

MaxGIRF
5.65%
5.65%
5.65%
5.65%
5.65%

700

Spiral Axial Scans

CG-SENSE

MaxGIRF w/o off-resonance map

MaxGIRF w off-resonance map

Cartesian reference

Off-resonance map

-30 -20 -10 0 10 20 30 isocenter off-isocenter at z = 75 mm without static off-resonance correction

Difference due to conc. fields

CG-SENSE (C)

MaxGIRF (M)

|C -M| x10 z = 0 mm z = 35 mm z = 87.5 mm z = 105 mm

1

0.9

0.8

0.7

0.6

0.5

0.4

0.3

0.2

0.1

0 x = 0.0 mm

NUFFT

King's method lowest-order terms

MaxGIRF (L) lowest-order, CP

MaxGIRF (F) full-order, CP

MaxGIRF (CG)

CG

|F - L| x200

|CG - NUFFT| x5

|CG - King| x5

|CG - L| x5

|L - King| x5

Difference images

IMAGE RECONSTRUCTION INCORPORATING MAXWELL FIELDS AND GRADIENT IMPULSE RESPONSE FUNCTION DISTORTION

CROSS-REFERENCE TO RELATED APPLICATIONS

This application is based upon and claims priority to U.S. provisional patent application 63/170,096 entitled "IMAGE RECONSTRUCTION INCORPORATING MAXWELL FIELDS AND GRADIENT IMPULSE RESPONSE FUNCTION DISTORTION" and filed on Apr. 2, 2021, the entire content of which is incorporated herein by reference.

STATEMENT AS TO FEDERALLY SPONSORED RESEARCH

This invention was made with government support under HL130494 awarded by the National Institutes of Health (NIH). The government has certain rights in this invention.

BACKGROUND

1. Field

This disclosure relates generally to image reconstruction technology, and more specifically, to image reconstruction incorporating Maxwell fields and gradient impulse response function distortion.

2. Description of the Related Art

Non-Cartesian imaging, particularly spiral imaging, has advanced continuously and current state-of-the-art in spiral imaging provides image quality comparable to a 2D/3D Cartesian counterpart in clinical MRI. Spiral acquisitions provide high scan efficiency and resistance to motion artifacts and therefore greatly used in various applications requiring rapid imaging such as MR Fingerprinting and Cardiac MRI.

However, spiral imaging is known to accrue undesired spatially varying phase caused by the concomitant field in addition to static off-resonance. The concomitant field, also known as Maxwell field, is additional nonrotating magnetic fields ($B_x$, $B_y$) generated in the reference frame whenever linear gradients are active. When the applied magnetic field strength is high (at least 0.55T), concomitant fields rotating in the counterclockwise direction in the rotating frame do not effectively nutate the spin but induce additional phase as the Bloch-Siegert effect. Thus, there remains a need for solutions for spiral imaging and solutions to ameliorate challenges associated with undesired spatially varying phase.

SUMMARY

An image reconstruction system is provided. The system may include a memory and a processor. The memory may be configured to store magnetic resonance imaging (MRI) data. The processor is coupled to the memory and may be configured to reconstruct a magnetic resonance imaging (MRI) image based on the MRI data and using an analytic concomitant field model to reduce distortion or disturbance in the reconstructed MRI image.

Various embodiments include one or more additional aspect as well. For example, the MRI data may be image data. The MRI data may be k-space data. To reconstruct the MRI image based on the MRI data and using the analytic concomitant field model, the processor is configured to use high-order concomitant field terms along with linear Fourier terms of the MRI data to reconstruct the MRI image more accurately than without the high-order concomitant field terms to reconstruct the MRI image. Using the high-order concomitant field terms in the reconstruction of the MRI image causes a reduction in local blurring of the MRI image and corrects or reduces artifacts in the MRI image to reduce distortion or disturbance in the reconstructed MRI image. The analytic concomitant field model identifies, uses and incorporates the high-order concomitant field terms in addition to the linear Fourier terms of the image data or the k-space data to reconstruct the MRI image. The processor is configured to reconstruct the MRI image further based on one or more receiver coil sensitivities of a MRI scanner that is used to capture the MRI data. To reconstruct the magnetic resonance imaging (MRI) image based on the MRI data and using the analytic concomitant field model, the processor is configured to calculate or determine an image vector or matrix that represents the reconstructed MRI image using a conjugate gradient algorithm or an iterative solver on the MRI data to recover the MRI image without artifacts.

The system may include an MRI scanner configured to obtain the MRI data of a patient. The processor may be configured to calculate spatial coordinates of a voxel of the MRI data in a physical coordinate system (PCS) including translating or rotating a location of the voxel in a reference coordinate system (RCS) to the PCS. The processor may be configured to apply a convolution of inputted nominal gradient waveforms or field with a gradient impulse response function (GIRF) to determine predicted or distorted gradient waveforms produced by gradient coils of the MRI scanner. The processor may be configured to apply the analytic concomitant field model computed with distorted gradient waveforms and voxels' physical coordinates to the MRI data.

The system may also include a display configured to output the reconstructed MRI image to a user. The processor may be configured to output, provide or render on the display the reconstructed MRI image to the user.

A method for reconstructing a magnetic resonance imaging (MRI) image is provided. The method may include obtaining, by a processor, MRI data of a patient. The method may include determining, by the processor, spatial coordinates of voxels of the MRI data in a physical coordinate system (PCS). The method may include applying a convolution of inputted nominal gradient waveforms with a gradient impulse response function (GIRF) to determine predicted or distorted gradient waveforms. The method may include applying the analytic concomitant field model computed with distorted gradient waveforms and voxels' physical coordinates to the MRI data. The method may include providing, by the processor, the MRI image to a user.

Various embodiments include one or more additional aspect as well. For example, the MRI data may be image data. The MRI data may be k-space data. Determining the spatial coordinates of the voxels of the MRI data in the PCS may include translating or rotating location of voxels in RCS to the PCS. The analytic concomitant field model may identify, use and incorporate high-order concomitant field terms in addition to linear Fourier terms of the MRI data to reconstruct the MRI image. Reconstructing the MRI image may be further based on one or more receiver coil sensitivities of a MRI scanner that used to capture the MRI data.

A non-transitory computer-readable medium is provided. The medium may include computer readable instructions, which when executed by a processor, cause the processor to perform operations. The operations may include obtaining image data or k-space data of a patient and calculating spatial coordinates of voxels in a physical coordinate system (PCS). The operations may include applying a convolution of inputted nominal gradient field waveforms with a gradient impulse response function (GIRF) to determine predicted or distorted gradient waveforms and applying the analytic concomitant field model computed with distorted gradient waveforms and voxels' physical coordinates to the image data or the k-space data. The operations may include providing a MRI image to a user.

Various embodiments include one or more additional aspect as well. To calculate the spatial coordinates of the voxels in the PCS the operations may include rotating or translating a location of the voxels in a matrix or reference coordinate system (RCS) to the PCS. In various embodiments, the analytic concomitant field model identifies, uses and incorporates high-order concomitant field terms in addition to linear Fourier terms of the image data or the k-space data to reconstruct the MRI image.

BRIEF DESCRIPTION OF THE DRAWINGS

Other systems, methods, features, and advantages of the present invention will be or will become apparent to one of ordinary skill in the art upon examination of the following figures and detailed description.

DETAILED DESCRIPTION

Figure 1:
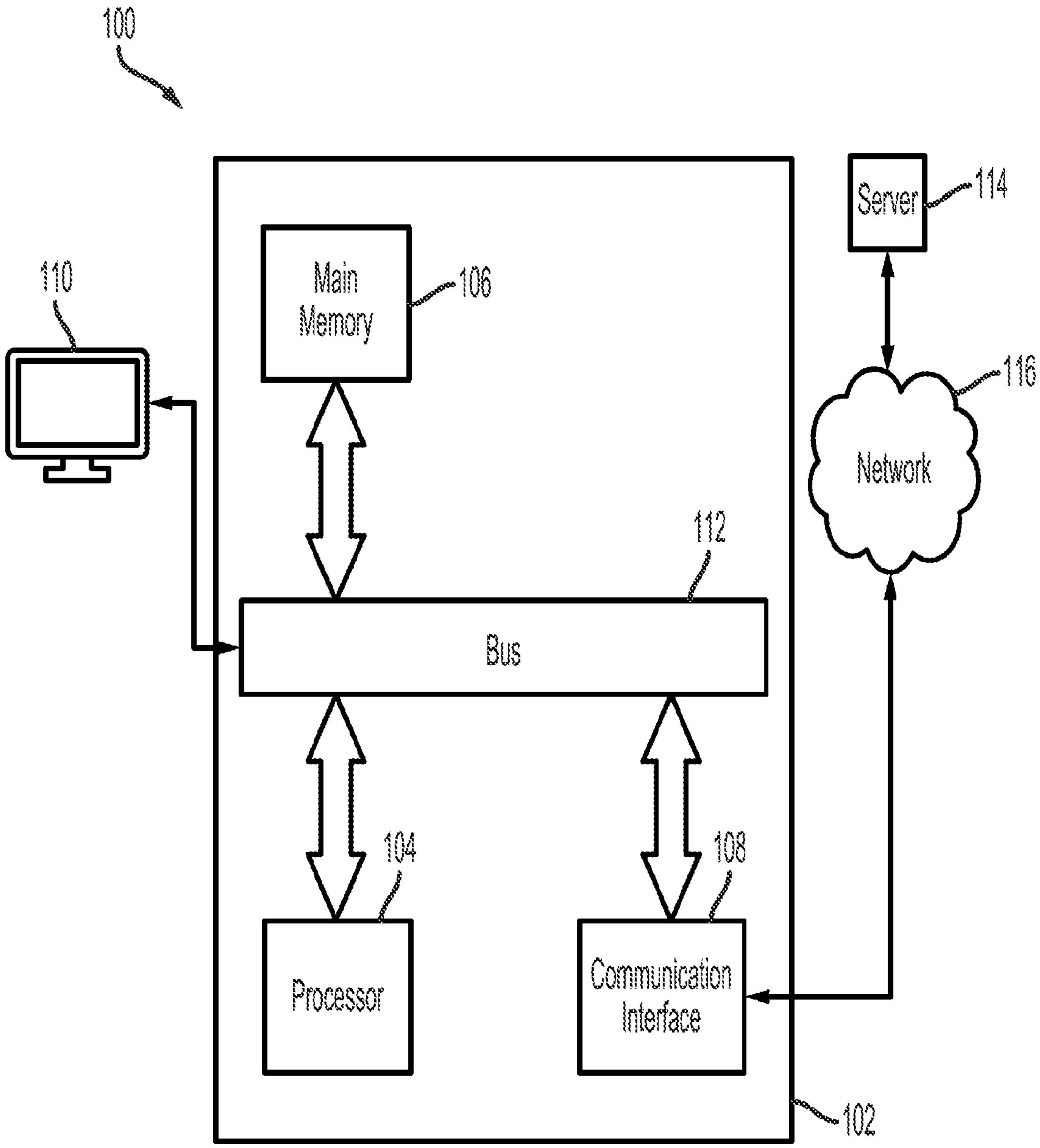
FIG. 1 shows an example block schematic diagram of a processing system employed to perform reconstruction of a Magnetic Resonance Imaging (MRI) image according to an aspect of the invention.

A system, apparatus and/or method for magnetic resonance imaging (MRI) reconstruction that mitigates local blurring caused by static off-resonance and concomitant fields. The MRI reconstruction system may use phantom-based gradient impulse response function (GIRF) measurements and analytic expressions to predict the concomitant fields.

Before addressing specific embodiments of the MRI reconstruction system with reference to the figures, this disclosure includes an instructive discussion of underlying operative principles implemented by the system. Non-Cartesian imaging, particularly spiral imaging, has advanced continuously and current state-of-the-art in spiral imaging provides image quality comparable to 2D/3D Cartesian counterpart in clinical MRI. Spiral acquisitions provide high scan efficiency and resistance to motion artifacts and therefore are used in various applications requiring rapid imaging such as MR fingerprinting and cardiac MRI.

However, spiral imaging is known to accrue undesired spatially varying phase caused by the concomitant field in addition to static off-resonance. The concomitant field, also known as the Maxwell field, is additional nonrotating magnetic fields ($B_x$, $B_y$) generated in the reference frame whenever linear gradients are active. When the applied magnetic field strength is high (at least 0.55T), concomitant fields rotating in the counterclockwise direction in the rotating frame do not effectively nutate the spin but induce additional phase as the Bloch-Siegert effect.

Initial efforts to provide solutions for spiral imaging to address this issue include image reconstructions and pulse sequence modifications. While successful, proposed image reconstructions are suboptimal because several approximations are applied to concomitant fields to increase computation speed.

Further efforts include incorporating higher-order dynamic fields to the encoding process. Such efforts demonstrate excellent image quality in various applications, including diffusion and structural imaging. A dynamic field camera comprising spatially distributed NMR field probes may be used to measure phase evolutions at various positions for field expansions with globally smooth functions. Although NMR field probes provide real-time monitoring of field evolutions from various sources, systems are fairly expensive and complex to build. Therefore, although promising, the higher-order approach relying on field-camera measurements may have limited success in clinical MRI.

In various embodiments, a functionally equivalent approach is to characterize gradient chains with gradient impulse response functions (GIRFs). Assuming a linear time invariant system for gradient chains, GIRFs capture gradient delays, eddy current effects, and mechanically induced field oscillations. For each gradient axis, an MR system is perturbed with a set of input gradients and field responses are measured with either a dynamic field camera or phantom-based methods. Field-camera measurements provide both self-responses and cross-responses (e.g., input gradient on the x-axis and field response on the y-axis), thereby allowing the full characterization of a multiple-input, multiple-output LTI system. On the other hand, phantom-based methods typically measure only self-term GIRFs and $B_0$ cross-terms. However, phantom-based GIRFs are proven to be effective in various applications, including RF pulse design, eddy current-induced artifact correction, and image reconstructions. Therefore, the phantom-based method is a reasonable compromise to an accurate, albeit expensive field monitoring device.

In various embodiments, gradients predicted with phantom-based GIRFs can better estimate concomitant fields than nominal gradients. As such, this disclosure proposes a novel image reconstruction method, denoted MaxGIRF, that incorporates higher-order Maxwell fields and GIRF trajectory corrections. This proposed method can be treated as "invisible" field probes that require no special hardware but GIRFs measured with phantom-based methods and a good analytic model of concomitant fields that depends on coil geometry and severity of gradient non-linearity. Non-Cartesian imaging with long readouts generally benefits from this method, but the impact of this method will be greatest at high-performance low-field systems because the strength of concomitant fields scales with the maximum gradient amplitude and inversely to the main magnetic field $B_0$.

The following discussion first validates the proposed method using noiseless simulations at various field strengths and off-center distances. Monte-Carlo numerical simulations of concomitant fields at various slice orientations are performed to provide a guideline for selecting a minimum rank when a low-rank approximation is applied to the MaxGIRF encoding model. MaxGIRF reconstructions using nominal and GIRF-predicted gradients are compared using a NIST/ISMRM system phantom acquired at 0.55T. Finally, MaxGIRF reconstructions are demonstrated on in vivo axial/sagittal datasets.

The correction approach is broadly divided into two classes: 1) the net phase of all isochromats within a voxel is zero prior to the next RF pulse and 2) the accrued net phase affects the spin phase after excitation or refocusing pulses in the following TR. The Type 1 class notably includes gradient-spoiled gradient-echo sequences (FISP, GRASS, FFE). The Type 1 class also comprises pulse sequences with no remaining transverse magnetization prior to the next RF pulse, including single-shot sequences, interleaved sequences with a long TR, and RF-spoiled gradient-echo sequences (FLASH, SPGR, T1-FFE). The Type 2 class includes balanced steady-state free precession (bSSFP) sequences and fast/turbo spin-echo (FSE, TSE) sequences.

Both gradients and spatial coordinates can be described either in the logical coordinate system or in the physical coordinate system. Subscripts (u, v, w)=(phase encoding (PE), readout (RO), slice selection (SL)) are used to indicate the logical coordinate system and (x, y, z) for the physical coordinate system. Unless clearly specified, the discussion utilizes the physical coordinate system exclusively.

Let "interleaf" count both the spiral interleaves and TR numbers in gradient-echo sequences. Using a modified version of the expanded signal model, the measured $\mathbf{k}$-space data over the region of interest $V \in \mathbb{R}^d$ with d=2,3 is expressed as:

$$d_{i,c}(t) = \int_V m(r)S_c(r)\exp(-j\phi_i(r, t))dr + n_{i,c}(t) = \langle m, e_{i,c}(\cdot, t)\rangle + n_{i,c}(t), \quad [1]$$

where $d_{i,c}$ denotes the i-th interleaf, c-th receive coil $\mathbf{k}$-space data of the target image m(r), $S_c(r)$ the spatial sensitivity at position r of the c-th coil, $\phi_i(r, t)$ the time-varying phase of a voxel at position r in radian, and $n_{i,c}$ the measurement noise. The symbol $\langle \bullet,\bullet \rangle$ is a shorthand notation for the inner product of two continuous functions of r. The indices i and c count the $N_i$ interleaves and $N_c$ receive coils, respectively. The MaxGIRF approach models the magnitude of the spatiotemporal magnetic field $\|B_i(r, t)\|_{\ell_2}$ as a sum of linear gradients $G_i(t)=(G_{x,i}(t), G_{y,i}(t), G_{z,i}(t))$ in Gauss per centimeter, static off-resonance $\Delta f(r)$ in hertz, and concomitant fields in tesla:

$$\|B_i(r, t)\|_{\ell_2} = G_i(t)\cdot r + 2\pi\Delta f(r)/\gamma + \sum_{\ell=1}^{N_\ell} h_{\ell,i}(t)p_\ell(r), \quad [2]$$

where $\ell$ counts the $N_\ell$ concomitant field terms, $p_\ell$ is the $\ell$-th concomitant field basis function (in $m^2$ or $m^3$) and $h_{\ell,i}$ is the $\ell$-th dynamic coefficient (in $T/m^2$ or $T/m^3$), expressed as a function of the i-th gradient waveforms, and $\gamma$ is the gyromagnetic ratio (in rad/sec/T).

Analytic expressions of $\{h_{\ell,i}(t)\}_{\ell=1}^{N_\ell}$ and $\{p_\ell(r)\}_{\ell=1}^{N_\ell}$ for a symmetric gradient system used in this study may be given. Also, note that linear gradients $G_i(t)$ can denote either GIRF-predicted gradients $$G_i^{pred}(t)$$

or nominal gradients $$G_i^{nom}(t).$$

The superscript is omitted for clarity. Time integration of the magnetic field multiplied by the gyromagnetic ratio $$\gamma,\ \gamma\int_0^t \|B_i(r, \tau)\|_{\ell_2} d\tau,$$

then gives the phase evolution of a voxel at position r as:

$$\begin{aligned}\phi_i(r, t) &= k_i(t)\cdot r + 2\pi\Delta f(r)t + \sum_{\ell=1}^{N_\ell} k_{\ell,i}(t)p_\ell(r), \\ &= k_i(t)\cdot r + \tilde{\phi}_i(r, t),\end{aligned} \quad [3]$$

where $k_{\ell,i}(t)$ is the $\ell$-th phase coefficient obtained by $$k_{\ell,i}(t) = Y\int_0^t h_{\ell,i}(\tau)d\tau,$$

and $\tilde{\phi}_i(r, t)$ denotes a phase term consisting of static off-resonance and concomitant fields. Let $N_k$ denote the number of $\mathbf{k}$-space samples per interleaf. Suppose that an underlying object can be represented as a weighted sum of N ideal voxel shapes, $$m(r) = \sum_{\rho=1}^{N} m_\rho i_\rho(r).$$

Inserting this representation into Equation 1 and discretizing in time leads to:

$$d_{i,c} = E_i S_c m + n_{i,c}, \quad [4]$$

where $d_{i,c}=[d_{i,c}(t_1), \ldots, d_{i,c}(t_{N_k})]^T \in \mathbb{C}^{N_k}$ contains the i-th interleaf, c-th coil measured $\mathbf{k}$-space data, $E_i \in \mathbb{C}^{N_k \times N}$ denotes the i-th encoding matrix, $S_c \in \mathbb{C}^{N \times N}$ is a diagonal matrix containing the spatial sensitivities of the c-th coil, $m=[m(r_1), \ldots, m(r_N)]^T \in \mathbb{C}^N$ is a vector of complex image values, and $n_{i,c}=[n_{i,c}(t_1), \ldots, n_{i,c}(t_{N_k})]^T \in \mathbb{C}^{N_k}$ contains the i-th interleaf, c-th coil measurement noise.

The (i-th) encoding matrix $E_i$ is expressed as the Hadamard product (element-wise multiplication, denoted $\circ$) of a Fourier matrix $F_i \in \mathbb{C}^{N_k \times N}$ containing only linear phase terms and a higher-order encoding matrix $H_i \in \mathbb{C}^{N_k \times N}$ containing other phase terms:

$$E_i = F_i \circ H_i, \text{ where} \quad [5]$$

$$F_i = \begin{bmatrix} \exp(-jk(t_1)\cdot r_1) & \cdots & \exp(-jk(t_1)\cdot r_N) \\ \vdots & \ddots & \vdots \\ \exp(-jk(t_{N_k})\cdot r_1) & \cdots & \exp(-jk(t_{N_k})\cdot r_N) \end{bmatrix}, \text{ and} \quad [6]$$

$$H_i = \begin{bmatrix} \exp(-j\tilde{\phi}_i(r_1, t_1)) & \cdots & \exp(-j\tilde{\phi}_i(r_N, t_1)) \\ \vdots & \ddots & \vdots \\ \exp(-j\tilde{\phi}_i(r_1, t_{N_k})) & \cdots & \exp(-j\tilde{\phi}_i(r_N, t_{N_k})) \end{bmatrix}. \quad [7]$$

Figure 4A:
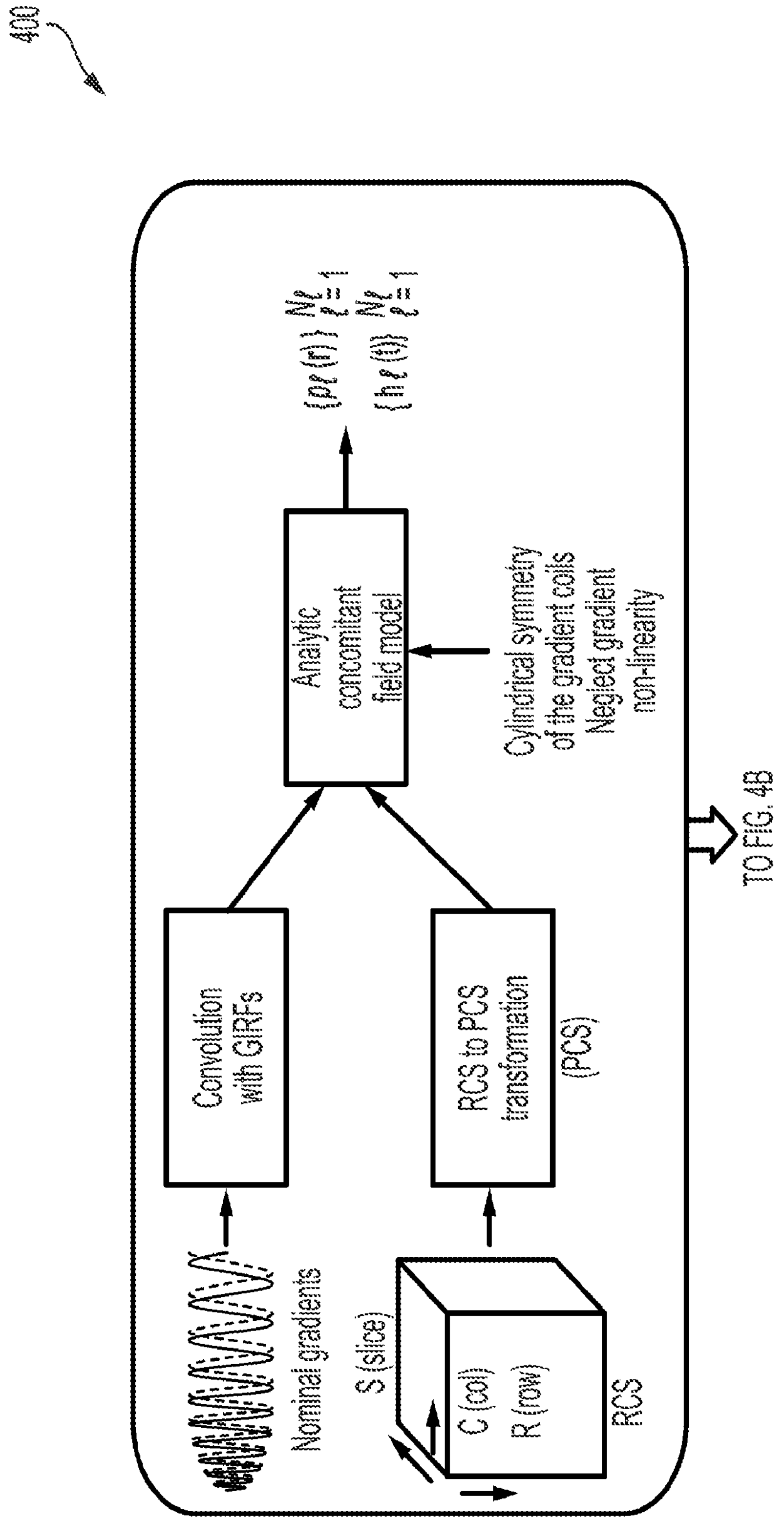
FIGS. 4A-B illustrates an example flow diagram of a process for reconstructing an MRI image and calculating associated encoding matrices according to an aspect of the invention.
Figure 4B:
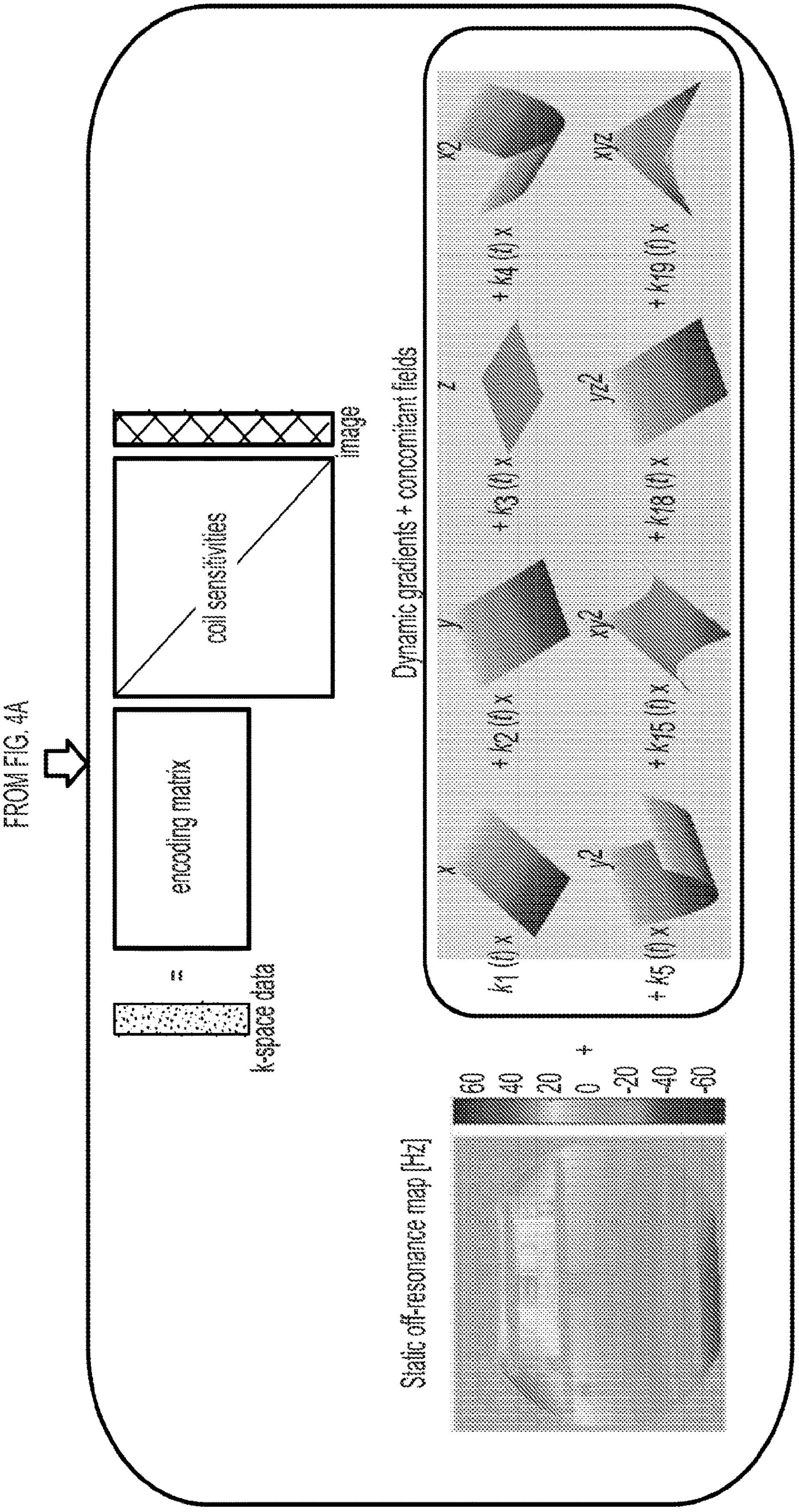

FIGS. 4A-B illustrate aspects of a process 400 of reconstructing an MRI image. FIGS. 4A-B include a visual depiction reiterating various aforementioned aspects of the disclosed mechanisms of calculating encoding matrices according to the MaxGIRF system and method herein. FIGS. 4A-B show that gradient waveforms in the logical coordinate system (LCS) are first transformed into the physical coordinate system (PCS). Distorted gradients in PCS are estimated by FFT-based convolution with phantom-based GIRFs after matching frequency resolution with zero-padding. Analytic expressions of concomitant fields derived from the coil geometry, presumed gradient non-linearity, and GIRF-predicted gradients, are for each spatial position in PCS. The phase evolution per voxel is represented as the sum of phase contributions from static off-resonance and spatial basis functions that includes both linear gradients and concomitant field terms. The MaxGIRF encoding model is an extension of the SENSE model that additionally includes phase terms due to static off-resonance and concomitant fields.

When distorted gradients are predicted with GIRFs and spatial coordinates in the physical coordinate system are calculated, several coordinate transformations are involved. This topic is detailed further below.

Various coordinate systems are used in an MR system that are essential to retrieve spatial coordinates in the physical coordinate system. Coordinate transformations are usually proprietary information and thus one may need to combine information from data headers of an ISMRM Raw Data (ISMRMRD) dataset, from scan prescriptions (scan orientation and rotation angle), and from reverse-engineering using a DICOM image and its corresponding set of DICOM spatial coordinates. Because both Cartesian (static off-resonance) and spiral acquisitions are needed for the MaxGIRF encoding model and both images must coincide in its matrix format, this section first describes coordinate transformations for 2D Cartesian imaging and later introduces modifications needed for spiral imaging. Monospace fonts are used to for parameters obtained from an ISMRMRD dataset.

Figure 5:
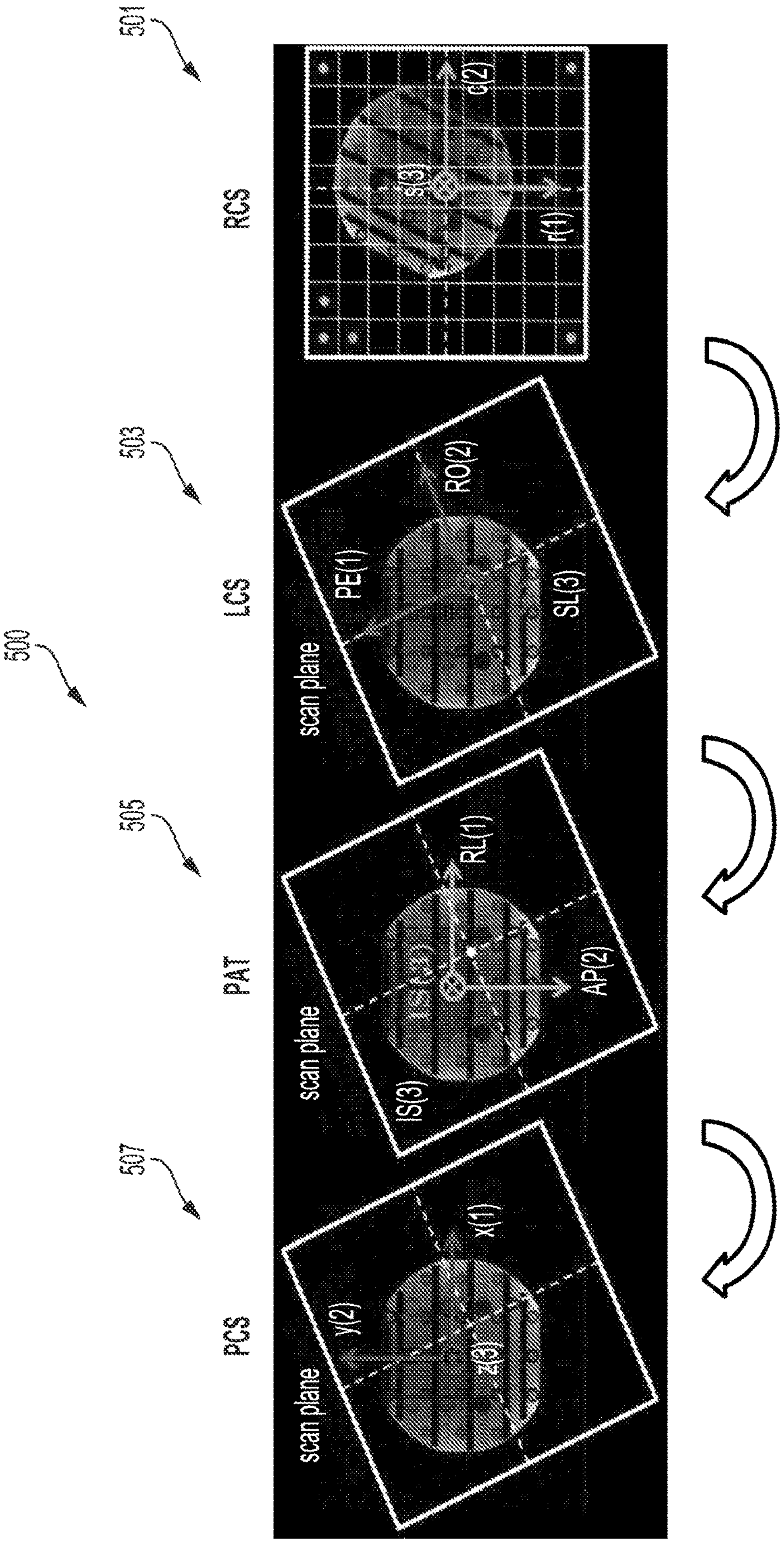
FIG. 5 provides an illustration of different coordinate transforms according to an aspect of the invention.

Various example coordinate transformations may be implemented for a patient in a head-first/supine position. FIG. 5 provides an illustration 500 of various of these coordinate transforms. For instance, the physical coordinate system (PCS) 507 used by the gradient system is fixed to a magnet and its origin is known as isocenter. The physical coordinate system for a particular MR system is usually provided in a vendor's proprietary software reference manual. The axes in the patient coordinate system (PAT) 505 are defined in right-left (RL), anterior-posterior (AP), and inferior-superior (IS) directions. A patient can have various bedding positions (e.g., head or feet first/prone, supine, decubitus right, or decubitus left), but the patient coordinate system is always fixed to the patient and shares its origin with the PCS. Therefore, a transformation from PAT 505 to PCS 507 is determined by patient position only. In an example case, the transformation from PAT 505 to PCS 507 is:

$$\begin{bmatrix} x \\ y \\ z \end{bmatrix} = \underbrace{\begin{bmatrix} 1 & 0 & 0 \\ 0 & -1 & 0 \\ 0 & 0 & -1 \end{bmatrix}}_{R_{PATtoPCS}} \begin{bmatrix} RL \\ AP \\ IS \end{bmatrix}. \quad [8]$$

After selecting a scan orientation (e.g., sagittal/coronal/axial), a scan plane can be rotated (described by a rotation angle), tilted (a slice normal vector), and have slice offsets. The axes in the logical coordinate system (LCS) 503 are defined in phase-encoding (PE), readout (RO), and slice selection (SL) directions. The origin of the LCS 503 is attached to the center of a scan plane and thus the transformation from LCS to PCS is a 3D rotation followed by a translation by slice offsets. This information can be obtained from the ISMRMRD dataset but for the system used in this study, modifications may be required to reflect gradient flips. The directions of gradients can be implicitly flipped as a function of a scan orientation and a rotation angle. Consequently, the storage order of measurements in an ISMRMRD dataset is flipped, and the corresponding dimension of an image is flipped. When gradient flips are introduced, it may be difficult to spatially register a custom reconstructed image with a DICOM image in the patient coordinate system. One way to achieve perfect registration is to reverse the storage order of any dimension that has been flipped and change the sign of the corresponding column in an LCS-to-PCS rotation matrix. For this purpose, the discussion introduces two parameters, "PE_sign" and "R0_sign," to indicate a gradient flip along PE and RO directions, respectively. For example, if "PE_sign"=−1, then the storage order of a matrix along the PE direction is reversed and the sign of the first column of a 3×3 LCS-to-PCS rotation matrix is flipped. These two parameters need to be reverse-engineered from datasets acquired with rotation angles ranging from −180° to 180° with 15° increment for each orientation. To summarize, the rotation matrix from LCS to PCS and slice offsets in the PCS can be described as:

$$\begin{bmatrix} RL \\ AP \\ IS \end{bmatrix} = \underbrace{\begin{bmatrix} \text{phase\_dir}[1] & \text{read\_dir}[1] & \text{slice\_dir}[1] \\ \text{phase\_dir}[2] & \text{read\_dir}[2] & \text{slice\_dir}[2] \\ \text{phase\_dir}[3] & \text{read\_dir}[3] & \text{slice\_dir}[3] \end{bmatrix} \begin{bmatrix} \text{PE\_sign} & 0 & 0 \\ 0 & \text{RO\_sign} & 0 \\ 0 & 0 & 1 \end{bmatrix}}_{R_{LCStoPAT}} \begin{bmatrix} PE \\ RO \\ SL \end{bmatrix}, \quad [9]$$

$$\text{PAT\_offset} = \text{position},$$

where head.phase_dir[3], head.read_dir[3], head.slice_dir[3] are the directional cosines of the readout, phase-encoding, and slice direction, respectively, and head.position[3] is the three-dimensional spatial offsets from isocenter. For spiral imaging, the phase-encoding gradient is multiplied with "PE_sign" and the readout gradient with "RO_sign" instead of changing the storage order. Equation 9 remains unaltered for spiral imaging.

When raw k-space data is read in a programming platform (e.g., MATLAB), each readout, phase-encoding, and slice-encoding direction is matched to each dimension of a 3D matrix. Determining the readout and phase-encoding directions is straightforward because an oversampling factor of 2 is usually used along the readout direction. In an example embodiment of FIG. 5, the readout direction (− to +) is aligned along the increasing direction of the first dimension (row) and the phase-encoding direction (− to +) along the increasing direction of the second dimension (column) and the slice-encoding along the third dimension (slice). The axes in the matrix coordinate system (RCS) 501 are row, column, and slice directions. The origin matches with LCS 503 and is located at the FFT center of an $N_1 \times N_2 \times N_3$ matrix, i.e., (floor($N_1$/2)+1, floor($N_2$/2)+1, floor($N_3$/2)+1) for index starting from 1. Each voxel is assigned matrix coordinates (r, c, s) where each coordinate ranges from −floor($N_\ell$/2) to ceil($N_\ell$/2)-1 for $\ell$=1,2,3. Then, the transformation from RCS 501 to LCS 503 is described by:

$$\begin{bmatrix} PE \\ RO \\ SL \end{bmatrix} = \underbrace{\begin{bmatrix} 0 & 1 & 0 \\ 1 & 0 & 0 \\ 0 & 0 & 1 \end{bmatrix}}_{R_{RCStoLCS}} \begin{bmatrix} r \\ c \\ s \end{bmatrix}. \quad [10]$$

Finally, matrix coordinates are scaled with voxel size and a series of transformations are applied to yield spatial coordinates (in m) in the physical coordinate system:

$$\begin{bmatrix} x \\ y \\ z \end{bmatrix} = R_{PATtoPCS} \cdot \left( R_{LCStoPAT} \cdot R_{RCStoLCS} \cdot R_{scaling} \cdot \begin{bmatrix} r \\ c \\ s \end{bmatrix} + \text{PAT\_offset} \right) \quad [11]$$

Image reconstruction for MaxGIRF encoding can be formulated as a (overdetermined) linear least-squares problem:

$$\hat{m} = \underset{m}{\operatorname{argmin}} \sum_{i=1}^{N_i} \sum_{c=1}^{N_c} \| d_{i,c} - E_i S_c m \|_{\ell_2}^2. \quad [12]$$

Equation 12 often needs to be expressed in the form of A(m)=b to be solved with iterative algorithms (e.g., LSQR implementation of the conjugate gradient method). Such a form is obtained by taking the derivative of a cost function with respect to m and set it equal to zero:

$$\sum_{i=1}^{N_i} \sum_{c=1}^{N_c} \left( A_{i,c}^H A_{i,c} \right) m = \sum_{i=1}^{N_i} \sum_{c=1}^{N_c} A_{i,c}^H (d_{i,c}), \quad [13]$$

where $A_{i,c}(x)=E_i S_c x$: $\mathbb{C}^N \to \mathbb{C}^{N_k}$ denotes the linear forward operator that maps a length-N vector of image values to a length-$N_k$ vector of k-space samples of the i-th interleaf and c-th coil, and $$A_{i,c}^H(y) = S_c^H E_i^H y: \mathbb{C}^{N_k} \to \mathbb{C}^N$$

denotes its adjoint. The superscript $(\bullet)^H$ denotes the transposed complex conjugate. Equation 13 can be related to the previous formulation of the expanded encoding model. All measured k-space data from all interleaves and coils may be stacked into a single measurement vector $d \in \mathbb{C}^{N_c N_i N_k}$. The sensitivity encoding operator E(m): $\mathbb{C}^N \to \mathbb{C}^{N_c N_i N_k}$ may be defined as:

$$\underbrace{\begin{bmatrix} d_{1,1} \\ d_{N_i,1} \\ d_{1,N_c} \\ d_{N_i,N_c} \end{bmatrix}}_{d} = \underbrace{\begin{bmatrix} A_{1,1} \\ A_{N_i,1} \\ A_{1,N_c} \\ A_{N_i,N_c} \end{bmatrix} m}_{E(m)} + \underbrace{\begin{bmatrix} n_{1,1} \\ n_{N_i,1} \\ n_{1,N_c} \\ n_{N_i,N_c} \end{bmatrix}}_{n}, \quad [14]$$

and its adjoint $E^H(d)$: $\mathbb{C}^{N_c N_i N_k} \to \mathbb{C}^N$ as:

$$E^H(d) = \begin{bmatrix} A_{1,1}^H & A_{N_i,1}^H & A_{1,N_c}^H & A_{N_i,N_c}^H \end{bmatrix} \begin{bmatrix} d_{1,1} \\ d_{N_i,1} \\ d_{1,N_c} \\ d_{N_i,N_c} \end{bmatrix} = \sum_{i=1}^{N_i} \sum_{c=1}^{N_c} A_{i,c}^H (d_{i,c}). \quad [15]$$

Using the sensitivity encoding operator E(•) and its adjoint $E^H(\bullet)$, the left side of Equation 13 can be expressed as:

$$\sum_{i=1}^{N_i} \sum_{c=1}^{N_c} \left( A_{i,c}^H A_{i,c} \right) m = \begin{bmatrix} A_{1,1}^H & A_{N_i,1}^H & A_{1,N_c}^H & A_{N_i,N_c}^H \end{bmatrix} \begin{bmatrix} A_{1,1} \\ A_{N_i,1} \\ A_{1,N_c} \\ A_{N_i,N_c} \end{bmatrix} m = E^H E(m), \quad [16]$$

and Equation 13 becomes $E^H E(m) = E^H(d)$, which is identical to the normal equation. Using this form, a conjugate gradient algorithm or LSQR is readily applicable.

To reduce the computation burden of explicit matrix-vector multiplications, a low-rank approximation to the higher-order encoding matrix $H_i$ may be proposed. This and other similar approaches enabled fast matrix-vector computations using fast Fourier transform (FFT). A similar approach to the MaxGIRF encoding model may be implemented. For example, the model may first represent a higher-order encoding matrix $H_i$ with its singular value decomposition (SVD) and derive a new expression of Equation 5 based on the SVD of $H_i$. Finally, a low-rank approximation using truncated SVD is applied to all higher-order encoding matrices.

Suppose the SVD of a higher-order encoding matrix $H_i$ is given by:

$$H_i = \sum_{\ell=1}^{L_{max}} u_{\ell,i} \sigma_{\ell,i} \tilde{v}_{\ell,i}^H = \sum_{\ell=1}^{L_{max}} u_{\ell,i} v_{\ell,i}^H, \quad [17]$$

where $\mathbf{u}_{\ell,i} \in \mathbb{C}^{N_k}$ denotes the $\ell$-th left singular vector, $\sigma_{\ell,i} \in \mathbb{R}$ the $\ell$-th singular value, $\tilde{\mathbf{v}}_{\ell,i} \in \mathbb{C}^N$ the $\ell$-th right singular vector, and $L_{max}$ is the true rank of the higher-order encoding matrix $H_i$. A singular value and the corresponding right singular vector can be combined to yield $\tilde{\mathbf{v}}_{\ell,i} \in \mathbb{C}^{N}$. The vectors $\mathbf{u}_{\ell,i} \in \mathbb{C}^{N_k}$ and $\tilde{\mathbf{v}}_{\ell,i} \in \mathbb{C}^{N}$ are hereafter referred to as spatial and temporal basis vectors for the i-th higher-order encoding matrix $H_i$, respectively. Note that the relation in Equation 17 is exact (no loss in accuracy) and $L_{max}$ is large (>50) in general. Substituting Equation 17 into Equation 5 yields:

$$E_i = F_i \circ \left(\sum_{\ell=1}^{L_{max}} u_{\ell,i} v_{\ell,i}^H\right) = \sum_{\ell=1}^{L_{max}} F_i \circ \left(u_{\ell,i} v_{\ell,i}^H\right) = \sum_{\ell=1}^{L_{max}} \mathrm{diag}(u_{\ell,i}) F_i \mathrm{diag}(v_{\ell,i}^*), \quad [18]$$

where $\mathrm{diag}(\mathbf{u}_{\ell,i}) \in \mathbb{C}^{N_k \times N_k}$ and $\mathrm{diag}(\mathbf{v}_{\ell,i}^*) \in \mathbb{C}^{N \times N}$ are diagonal matrices containing the elements of the vectors $\mathbf{u}_{\ell,i}$ and $\mathbf{v}_{\ell,i}^*$ (the complex conjugate of $\tilde{\mathbf{v}}_{\ell,i}$) in the main diagonal, respectively. The last expression is obtained using the special property of the Hadamard product of a dense matrix $F_i$ with a rank-1 matrix $\mathbf{u}_{\ell,i}\mathbf{v}_{\ell,i}^H$. Using Equation 18, the forward and adjoint operators can be expressed as:

$$A_{i,c}(x) = E_i S_c x = \sum_{\ell=1}^{L_{max}} \mathrm{diag}(\tilde{u}_{\ell,i}) F_i \mathrm{diag}(v_{\ell,i}^*) S_c x, \quad [19a]$$

$$A_{i,c}^H(y) = S_c^H E_i^H y = S_c^H \sum_{\ell=1}^{L_{max}} \mathrm{diag}(v_{\ell,i}) F_i^H \mathrm{diag}(u_{\ell,i}^*) y. \quad [19b]$$

Equation 19a indicates that an expensive, explicit matrix-vector multiplication with an encoding matrix $E_i$ can be replaced by $L_{max}$ summations of a fast routine because the multiplication of a non-Cartesian Fourier matrix $F_i$ with a vector can be performed efficiently by FFT followed by inverse gridding or non-uniform fast Fourier transforms (NUFFT). Similarly, in Equation 19b, its adjoint $$E_i^H$$

can be performed by $L_{max}$ summations of gridding followed by inverse FFT or the adjoint of NUFFT. $\mathbf{k}$-space sampling density correction is usually performed before gridding and the adjoint of NUFFT. This formulation reduces the memory footprint drastically from a hundred gigabytes (GB) to a few GBs for high-resolution, long readout non-Cartesian datasets. More importantly, this formulation allows smooth integration of the MaxGIRF encoding model with existing gridding or NUFFT based non-Cartesian reconstruction routines provided in reconstruction platforms such as BART, Gadgetron, and GPI. When performing NUFFT or the adjoint of NUFFT, k-space trajectories in the RCS must be used. This can be achieved by applying the inverse of a RCS-to-LCS transformation on logical k-space trajectories as $\mathbf{k}_{RCS,i}(t)=(R_{RCStoLCS})^{-1}\cdot\mathbf{k}_{LCS,i}(t)$.

Here the system may apply a low-rank approximation to the higher-order encoding matrix $H_i$. According to the Eckart-Young theorem, the rank-L SVD truncation $\hat{H}_i=\sum_{\ell=1}^{L}\mathbf{u}_{\ell,i}\mathbf{v}_{\ell,i}^H$ provides the best rank-L approximation to $H_i$ in a least-squares sense:

$$\|H_i - \hat{H}_i\|_F = \underset{rank(B)\le L}{\mathrm{argmin}} \|H_i - B\|_F = \sqrt{\sigma_{L+1}^2 + \ldots + \sigma_{Lmax}^2}. \quad [20]$$

Only one L is selected and the summation is truncated from $L_{max}$ to L across all higher-order encoding matrices.

Equation 1 uses the definition of a forward Fourier transform widely used in signal processing community. However, different vendors use different conventions of the Fourier and inverse Fourier transform pair. For this study, an inverse Fourier transform (i.e., $\exp(+j\phi_i(r, t))$) is actually used and the forward Fourier transform is used to reconstruct an image from $\mathbf{k}$-space data. It is important to use the same FT/IFT convention as the vendor of a chosen MR system when performing the MaxGIRF reconstruction. Because different vendors reconstruct DICOM images with different definitions of a FT/IFT pair, reverse-engineering coordinate transformations considering the DICOM information as the ground truth becomes infeasible. The definition of NUFFT is the same as what is used in Equation 1. To use the opposite definition, a sign flip on k-space trajectories, $\mathbf{k}_{RCS,i}(t)\rightarrow-\mathbf{k}_{RCS,i}(t)$, can be used.

For reconstruction and image processing, Cartesian and spiral image reconstructions and post-processing may be implemented. For both Cartesian and spiral reconstructions, FFT was applied to transform from $\mathbf{k}$-space to image space. Coil sensitivity maps were estimated using the Walsh method from the 32×32 Hanning-windowed center of $\mathbf{k}$-space data (gridded $\mathbf{k}$-space data for spiral acquisitions). Both intensity normalization and gradient nonlinearity correction were not applied. Spiral trajectories were generated using software. A sample density compensation function was computed. For static off-resonance map calculation, phase difference images relative to the first echo were reconstructed. Noise background was removed with intensity thresholding. An optimum threshold for noise background was calculated using an iterative algorithm applied to the maximum intensity of all echo images. After thresholding all echo images, a linear least-squares fitting was performed to calculate a raw static off-resonance map in Hz on a pixel by pixel basis. An intensity-weighted, global spherical harmonic fitting was performed to approximate void regions with non-zero off-resonance values within the object. After replacing void regions with a spherical harmonic fit, a smoothed static off-resonance map was obtained with total generalized variation (TGV) denoising with a regularization parameter of 10 and 2000 iterations for the primal-dual algorithm.

A commonly used method to truncate the SVD is to truncate at a rank L that captures a certain amount of its energy. A minimum L based on 99% cutoff was selected. For each slice orientation (sagittal/coronal/axial/oblique), Monte Carlo simulations of various off-isocenter distances were performed. The off-isocenter distance was linearly varied from −200 mm to +200 mm in increments of 4 mm (100 realizations). For the oblique orientation, a slice normal vector was only varied randomly at isocenter. A randomized SVD algorithm as implemented in was used to compute the SVD of a higher-order encoding matrix. Singular values up to 250 and its cumulative energy spectrum were calculated for each realization. Since this stringent cutoff criterion may be relaxed for some applications, this effort also investigated the effect of lowering L on MaxGIRF reconstruction of a sagittal slice at isocenter using two metrics: (1) normalized root mean square error (NRMSE) between full-rank and L-rank reconstructions for magnitude and phase images separately, $$NRMSE_m = \| |m_{full}| - |m_L| \|_{\ell_2} / \|m_{full}\|_{\ell_2} \text{ and}$$

$$NRMSE_p = \| \angle m_{full} - \angle m_L \|_{\ell_2} / \| \angle m_{full} \|_{\ell_2},$$

and (2) maximum phase deviation between full-rank and L-rank reconstructions (max deviation)=max$|\angle m_{full} - \angle m_L|$. Image reconstructions were performed using noiseless brain simulations.

To validate the proposed MaxGIRF approach, noiseless simulations on 256×256 brain images with simulated 8-channel coil sensitivity maps were performed. Three (sagittal/coronal/axial) slices were obtained from a 3D MIDA brain phantom and coil sensitivity maps were obtained. The 480×480×350 MIDA phantom provides 116 tissue types and these were categorized into 13 tissue labels used in a Brainweb phantom by visual matching (background, CSF, grey matter, white matter, fat, muscle/skin, skin, skull, glial matter, meat, blood, bone marrow, and cartilage). MR parameters ($T_1/T_2/T^*_2/M_0$) were obtained from a Brainweb phantom acquired at 1.5 T and the dependence of relaxation parameters on the main magnetic field strength was ignored. Parameter maps of size 480×480×350 were first generated and then resized to 256×256×256 using a 3D linear interpolation. An 8-interleaf, uniform-density spiral acquisition (26 msec readout) was simulated. Direct matrix-vector multiplications using Equations 4 and 5 were used to generate noiseless k-space data. System imperfections such as static off-resonance and eddy currents were not simulated. The B0 dependence (0.55T, 1.5T, 3T, 7T) and off-isocenter dependence (z=0, 50, 100, 150, 200 mm) of concomitant fields were simulated. MaxGIRF reconstructions were performed with a low-rank approximation (L=15/50 for axial/sagittal) and NUFFT. The NRMSE between a Cartesian reference and spiral reconstructions were calculated.

All imaging experiments were performed on a high-performance 0.55T scanner (prototype MAGNETOM Aera, Siemens Healthcare, Erlangen, Germany) with gradients capable of 45 mT/m amplitude and 200 T/m/s slew rate. A 16-channel head/neck receive coil was used for phantom and in-vivo experiments.

GIRF measurements were obtained using a set of triangular input functions and a spherical phantom. A body coil was used for both RF transmission and signal reception. The Brodsky method was used to estimate both $B_0$ cross-terms and first-order self-term GIRFs. In various instances, self-term GIRFs were used.

Spiral scans (axial and sagittal) of a NIST/ISMRM system phantom were acquired with a 2D GRE pulse sequence. An 8-interleaf, uniform-density spiral-out trajectory was designed to have 11.8 ms readout duration. The spiral trajectory rotated 360/8=45° every TR. A target axial slice was imaged at isocenter and 75 mm from isocenter. A sagittal slice was imaged at isocenter. Imaging parameters were: FOV=224×224 mm$^2$, resolution=1.4×1.4 mm$^2$, slice thickness=8 mm, flip angle=20°, TR=100 ms, TE=1 ms, and number of signal averages=1. Ten repetitions were performed to reach steady-state. For static off-resonance map calculation, 2D Cartesian gradient-echo sequences were used to acquire scans at multiple echo times (2.5, 3.7, 4.7, 5.7, 6.7, and 7.7 ms) with the same parameters as the spiral scans.

In-vivo human brain scans (axial and sagittal) were acquired with a 2D interleaved multi-slice spiral spin-echo pulse sequence. A slice-rephasing gradient and the left crusher of a refocusing pulse were combined with a waveform reshaping technique to minimize the concomitant-field phase accrual. Spoiler gradients were applied on all three axes at the end of a readout. Imaging parameters were: FOV=240×240 mm$^2$, resolution=0.75×0.75 mm$^2$, slice thickness=5 mm, slice gap=15 mm, flip angle=90°, TR=745 ms, TE=15 ms, and number of signal averages=10.

Figure 6A:
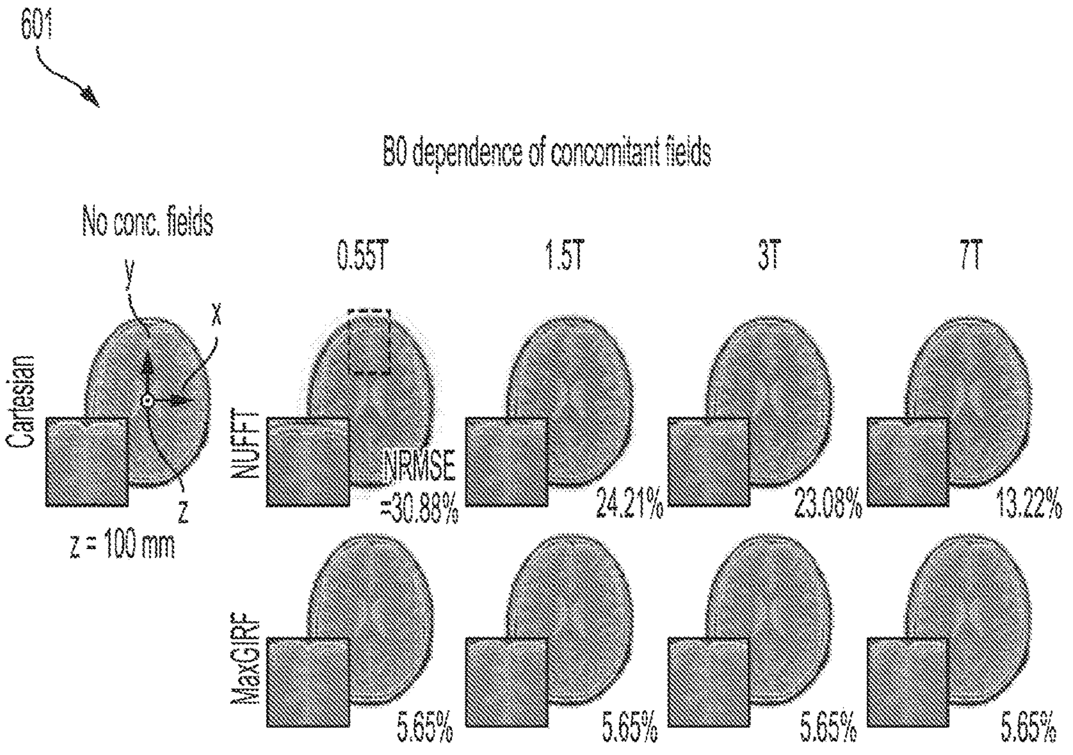
FIGS. 6A-B illustrate noiseless numerical simulations of MRI image reconstruction according to an aspect of the invention.
Figure 6B:
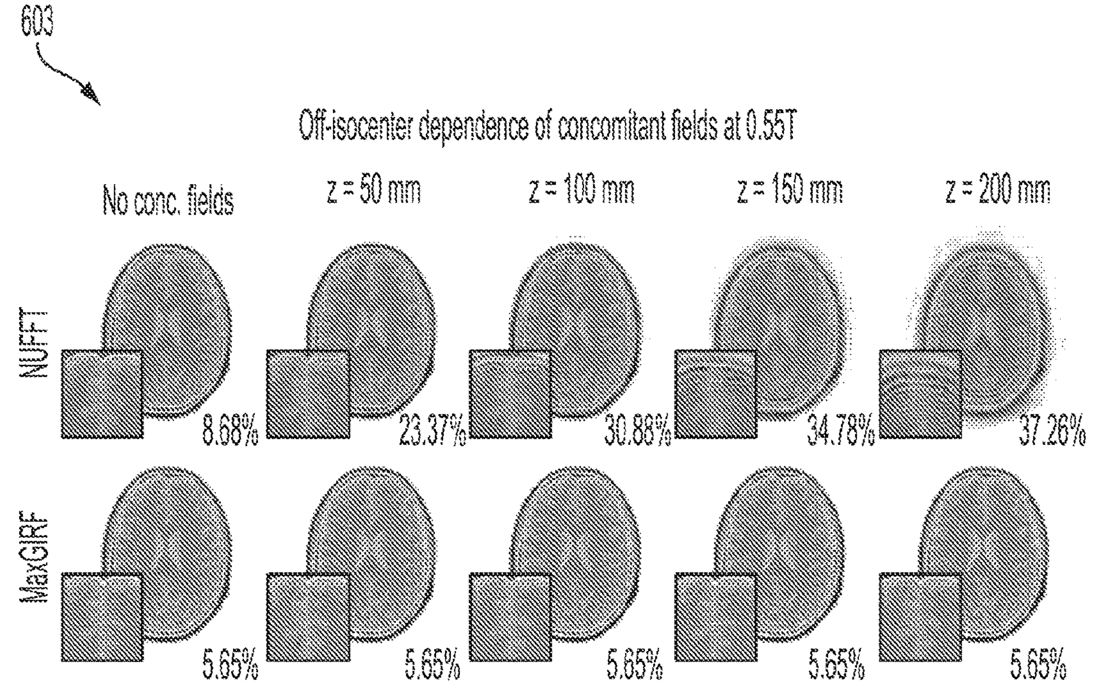

With reference to FIGS. 6A and 6B, noiseless numerical simulations 601, 603 of MaxGIRF reconstruction were demonstrated. The NRMSE (5.65%) for MaxGIRF at z=0 mm with B0=0.55T has a minimum achievable error, which is solely due to the difference between Cartesian and spiral image reconstructions since the concomitant field (FIG. 6A) becomes zero at isocenter for axial orientation. Application of MaxGIRF reconstruction off-isocenter (FIG. 6B) achieved this minimum error, indicating perfect correction of the concomitant fields. More specifically, FIGS. 6A-B illustrate evaluation of MaxGIRF reconstruction using ideal noiseless numerical simulations. These illustrations include depictions of a dependence of concomitant fields on B0, using field strengths (0.55T, 1.5T, 3T, 7T). A reference image used to simulate non-Cartesian k-space data is shown along with the physical coordinate system. The NRMSE between the ground truth and spiral reconstruction is shown, with 5.65% being the minimum achievable error solely from the difference between Cartesian and spiral image reconstruction. Dependence of concomitant fields on off-isocenter distance are demonstrated for axial prescription. NUFFT reconstruction shows increased spatial blurring as the field strength decreases and the distance from isocenter increases. Notice that all MaxGIRF reconstructions achieved the same minimum error (5.65%).

Figure 7:
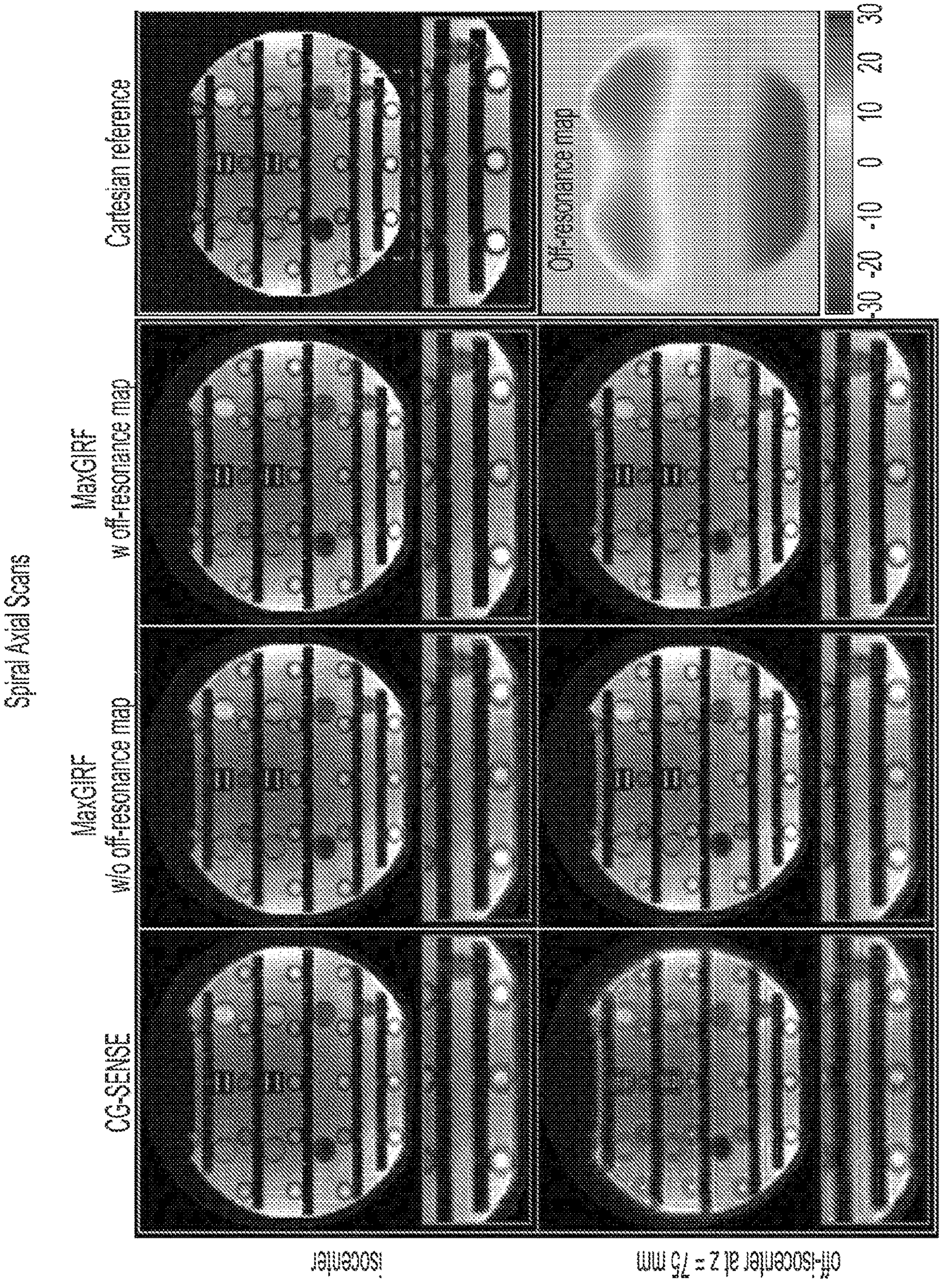
FIG. 7 illustrates MRI image reconstruction on axial spiral scans of a NIST/ISMRM phantom according to an aspect of the invention.

With reference to FIG. 7, an illustration 700 of MaxGIRF reconstruction on axial spiral scans of a NIST/ISMRM phantom at 0.55T shows excellent performance. Spiral axial imaging of a NIST/ISMRM phantom at 0.55T is shown with top row isocenter and bottom row off-isocenter with z=75 mm. A 2D Cartesian GRE reference is also shown (TE and SNR are not matched). CG-SENSE (1st column) clearly shows spatial blurring caused by both concomitant fields and static off-resonance. MaxGIRF can be applied without (2nd column) and with (3rd column) a separately acquired static off-resonance map. MaxGIRF without a static off-resonance map dramatically improves the image quality from CG-SENSE and further improvements are achieved with a static off-resonance map (one exemplary region shown in the box).

Figure 8:
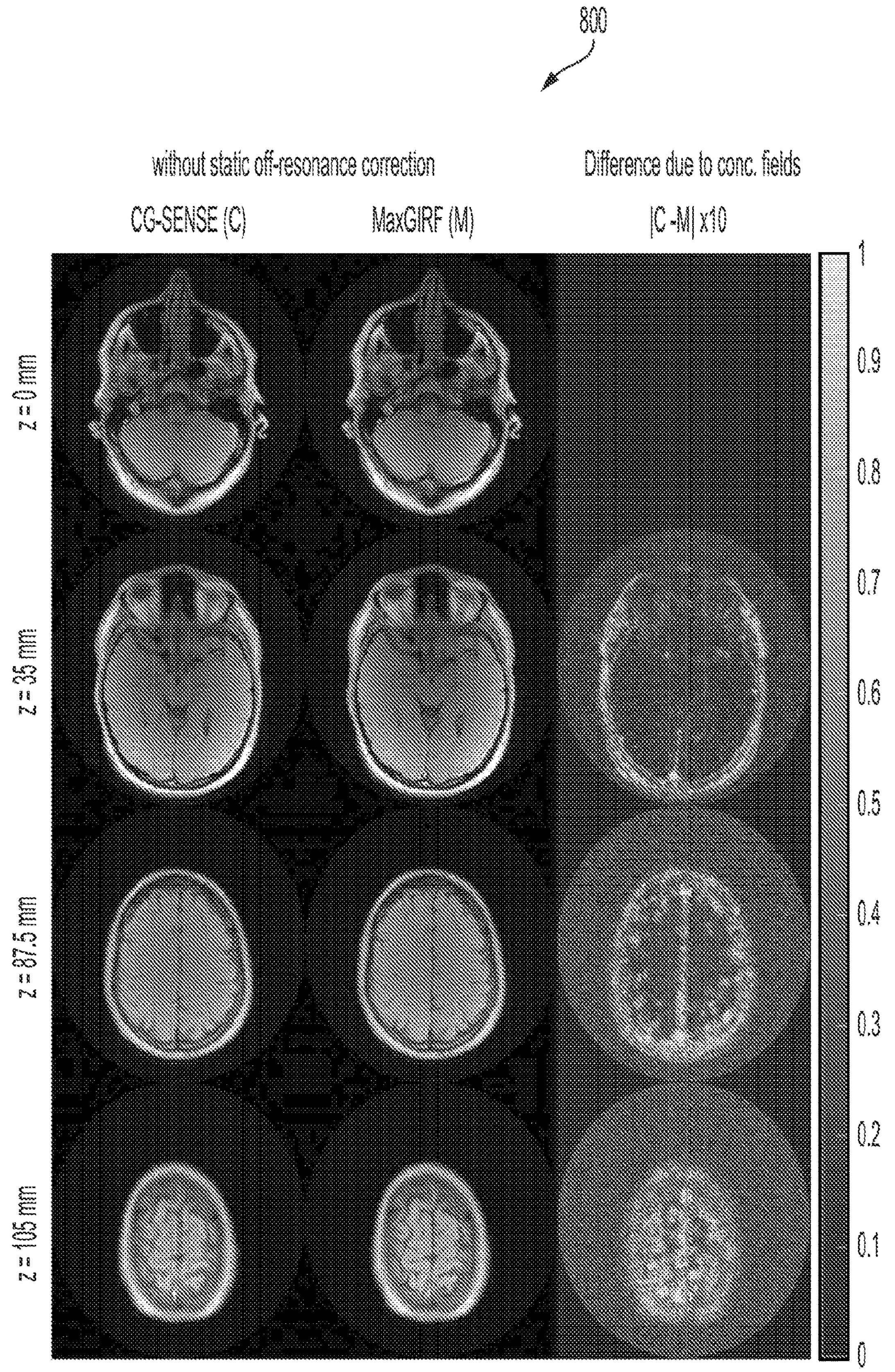
FIGS. 8-9 illustrate MRI image reconstruction on scans of a human volunteer according to an aspect of the invention.
Figure 9:
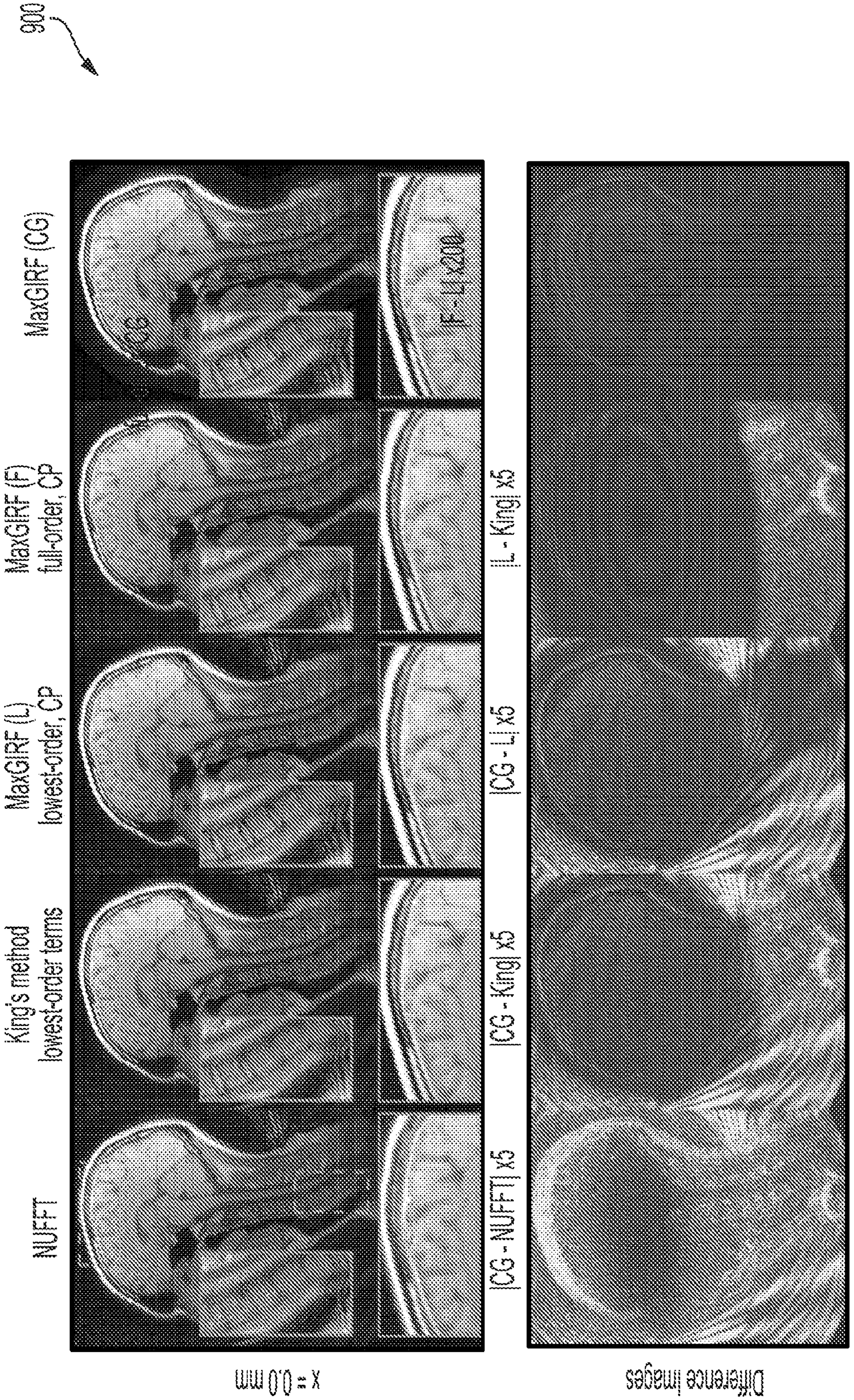

With reference to FIGS. 8-9, a first set of illustrations 800 and a second set of illustrations 900 of scans of a human volunteer at 0.55T show excellent performance. The blurring caused by the static off-resonance and concomitant fields is successfully removed as compared to conventional CG-SENSE reconstruction. The improvement in concomitant field blurring is evident in away from isocenter, as expected. The proposed reconstruction required 2 hours per slice (15 CG iterations×450 sec per iteration) using a quad-core, 20 GB RAM laptop.

FIG. 8 illustrates multi-slice axial spiral imaging of a healthy volunteer at 0.55T (left) CG-SENSE reconstructions. FIG. 8 illustrates, at middle, MaxGIRF reconstructions without static off-resonance correction (i.e., without a field map). FIG. 8 illustrates, at right, absolute difference images. GIRF-predicted gradients were used in both reconstructions. Static off-resonance correction was not performed, in order to isolate the difference due to concomitant field correction.

FIG. 9 illustrates mid-sagittal spiral imaging of a healthy volunteer at isocenter at 0.55T, showing (1st) NUFFT, ($2^{nd}$) King's method, ($3^{rd}$) MaxGIRF with lowest order terms and conjugate phase reconstruction, ($4^{th}$) MaxGIRF with full order terms and conjugate phase reconstruction, ($5^{th}$) MaxGIRF with full order terms and CG-SENSE reconstruction (Bottom). GIRF-predicted gradients were used in both reconstructions. Static off-resonance correction was not performed, in order to isolate the difference due to concomitant field correction. The spiral trajectory was designed for 224×224 $mm^2$ FOV and reconstructed at twice the FOV with the same spatial resolution, which causes the aliasing at the back of the neck. MaxGIRF reconstructions were able to compensate strong concomitant fields near the neck region (see the illustrated box). King's method shows residual concomitant fields when compared with (non-iterative) conjugate phase-based MaxGIRF reconstruction.

MaxGIRF improves the sharpness of spiral acquisitions. Here the method is demonstrated using axial slices acquired at off-isocenter and peripheral regions of sagittal slices and will be applicable for low and high-field imaging.

MaxGIRF estimates higher-order fields without NMR field probes but with theoretically derived analytic expressions of concomitant fields, which depend on coil geometry and gradient non-linearity. In some instances, zero gradient non-linearity was presumed but with image distortions. In various embodiments, gradient non-linearity could be incorporated with the MaxGIRF framework or post-hoc vendor corrections can be separately applied.

Moreover, reconstruction time may be enhanced, such as for 3D and/or very high-resolution spiral scans, by parallel computing of NUFFTs via openMP (many cores) or multiple GPUs. Moreover, in various instances, acquisitions may be considered where the accrued net phase affects the spin phase after excitation or refocusing pulses in the following TR. This specifically includes bSSFP and FSE sequences.

Thus, the preceding discussion illustrates a computational image reconstruction that incorporates concomitant fields (Maxwell fields) and gradient impulse response distortion. Substantially improved image quality are achieved for long-readout spiral imaging at low field. The impact may be greatest when imaging with longer readouts and/or at lower field strength.

Figure 2:
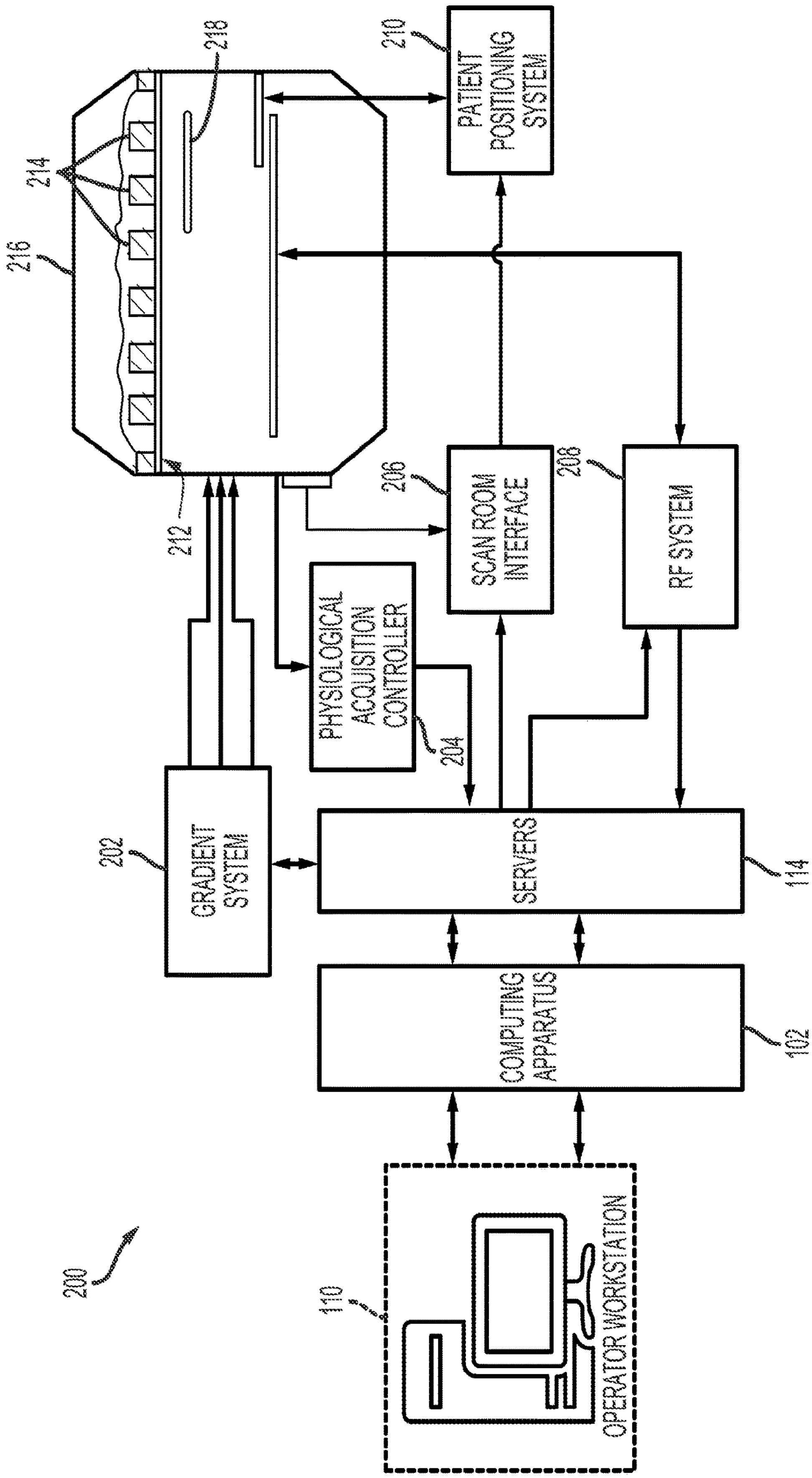
FIG. 2 shows an example block schematic diagram of an MRI system according to an aspect of the invention.
Figure 3:
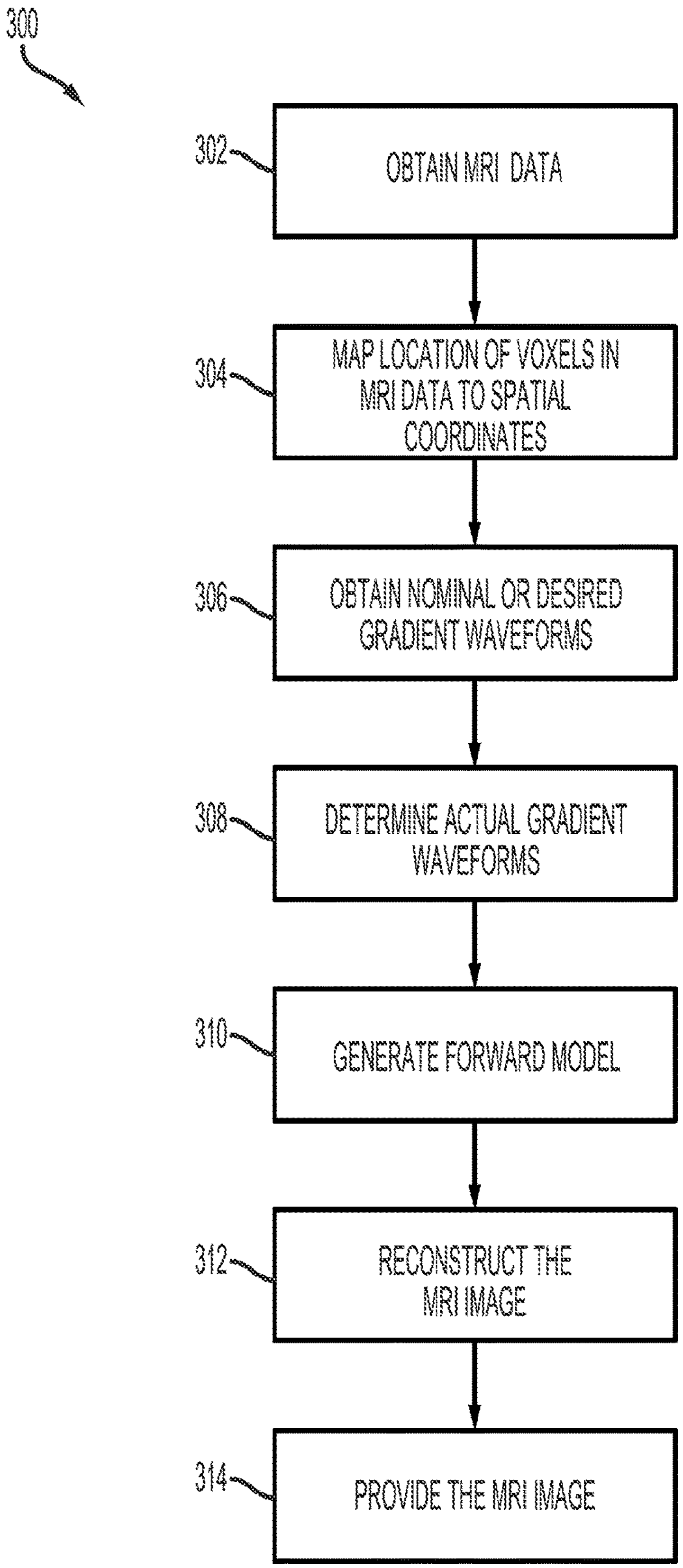
FIG. 3 is an example flow diagram of a process for reconstructing an MRI image according to an aspect of the invention.

Before shifting to a discussion of example embodiments illustrated in FIGS. 1-3, a helpful summary of various beneficial features of the disclosed system is useful. For instance, MRI with non-Cartesian data sampling can suffer from image blurring caused by static off-resonance and concomitant fields. Concomitant fields are especially problematic when using prolonged non-Cartesian acquisitions with high gradient amplitudes at lower field strengths, and for locations far from the MRI scanner's isocenter. The proposed MaxGIRF approach provides a cost-effective and accurate solution to this burring.

One beneficial feature of the proposed MaxGIRF approach is that it incorporates concomitant field effects. MRI reconstruction typically ignores concomitant field effects, and users tolerate the blurring. By incorporating concomitant field effects, the proposed methods produce more well-defined images, and allows greater methodologic flexibility. MRI systems behave as a low-pass filter and play distorted gradient waveforms with different delays during imaging. Concomitant fields are generated when these gradient waveforms are active. It is well known that a mismatch between theoretical and actual gradient waveforms causes image degradation for non-Cartesian imaging. Therefore, concomitant fields are estimated with greater accuracy using distorted gradient waveforms compared with theoretical gradient waveforms. A previous approach considers only gradient delays and use such predicted waveforms to correct simplified concomitant fields obtained with approximations. In contrast, the MaxGIRF approach utilizes gradient impulse response functions to predict gradient waveforms that are played during imaging and use such gradient waveforms to estimate concomitant fields without approximations. Therefore, the proposed method corrects local blurring more accurately compared with previous methods that incorporate simplified concomitant fields.

Another beneficial feature is that the proposed approach enables low-field, long-readout, and off-center scanning. By incorporating concomitant fields during image reconstruction, it is possible to leverage the newfound methodologic flexibility to image at lower B0 field strengths, use longer (e.g., more time-efficient) readouts, and image further from the magnet's isocenter (e.g., enabling imaging with a large field-of-view, for instance the entire abdomen). The strength of concomitant fields scales with the maximum gradient amplitude, distance from isocenter, and inversely to the main magnetic field BB0. The severity of local burring increases as the readout duration gets longer. Even for a moderate readout duration of 11.8 msec, an off-center axial slice and a sagittal slice show severe blurring. Therefore, the MaxGIRF approach enables non-Cartesian imaging with long readouts at high-performance low-field systems, where SNR-efficient spiral acquisitions are attractive. The MaxGIRF also enables off-center scanning, which is necessary in cardiac, shoulder, or abdominal imaging.

Yet another beneficial feature is that the approach avoids the need for NMR field probes. The current state-of-the-art method for incorporating concomitant fields employs real-time monitoring using dynamic field cameras (also called "NMR field probes"), which is expensive, cumbersome, and requires separate technology development. The proposed method uses simulation and is not dependent on such additional hardware. A dynamic field camera consists of spatially distributed NMR field probes and measures phase evolutions inside the MRI due to higher order eddy currents, concomitant fields, and field fluctuations due to system heating and unknown sources. Commercially available systems (Skope Magnetic Resonance Technologies AG) are expansive and thus limiting its wide use in clinics. A functionally equivalent approach is to characterize gradient chains with gradient impulse response functions (GIRFs). Phantom-based GIRFs do not require additional hardware but only software (and a phantom) and are proven to be effective in various applications. Therefore, the MaxGIRF approach employing phantom-based GIRFs avoids the need for NMR field probes. Since advances in GIRFs include characterizing the temperature dependence of MRI systems and higher order eddy current fields, the performance of the MaxGIRF approach will advance as advanced phantom-based methods are employed.

The preceding discussion includes a demonstration of MaxGIRF for a symmetric cylindrical MRI configuration, which is the most common commercial configuration. MaxGIRF may be modified to work for other configurations where there is a model for the concomitant fields, enabling their simulation. Conventional MRI systems use a symmetric configuration of x and y gradient coils, where x and y gradient coils are identical but rotated by 90 with respect to each other. However, some commercial MRI systems employ asymmetric gradient coils which can be beneficial in some scenarios. Concomitant fields for asymmetric gradient coils are also well characterized by analytic expressions. Therefore, the MaxGIRF approach are readily applicable to such MRI systems using concomitant field terms for asymmetric gradient coils.

Moreover, the cost function in MaxGIRF could be augmented with regularization, which is helpful in cases where there is limited signal-to-noise, accelerated data acquisitions for faster imaging, or image properties that can be leveraged. Advanced MRI reconstruction methods often add additional terms to the cost function to incorporate a prior knowledge of an image. This leads to improved image reconstruction when data acquisition is accelerated. The MaxGIRF approach can incorporate sparsity promoting regularization terms such as 11 norm, total variation (TV), and total generalized variation (TGV) along with Tikhonov regularization. Sparsity along extra dimensions (e.g., temporal dimension) can be exploited to accelerate dynamic imaging such as speech, cardiac, and quantitative imaging.

Other algorithms may be implemented by the system for solving the inverse problem. The demonstration utilized nonlinear conjugate gradient (NLCG) to solve the cost function. There are many different solvers that could also be used. A cost function is solved with an iterative algorithm. When a regularization term is added, a set of optimal algorithms exist for the cost function with a particular choice of the regularization term. Therefore, when compressed sensing is combined with the MaxGIRF, many sparse recovery algorithms such as nonlinear conjugate gradient (for 11 norm), primal-dual (for TGV), fast iterative shrinkage thresholding (FISTA), Nestrov's accelerated algorithms (NESTA) could be used for solving the modified cost function. Variants of conjugate algorithms such as LSQR and LSMR are applicable to the cost function without regularization terms. To overcome the semi convergence behavior of conjugate gradient algorithms, a hybrid LSMR algorithm can be used for the cost function with Tikhonov regularization.

Finally, accurate quantitative imaging at low field based on non-Cartesian imaging is possible. The demonstration was for gradient echo imaging. MaxGIRF could also be applied to a variety of other imaging methods that are more quantitative in nature (for example MRF, Wave-CAIPI, etc.). MR fingerprinting (MRF) is a recent quantitative imaging using non-Cartesian k-space trajectories. MRF induces dynamically varying image contrast with a random flip angle pattern and collects many image frames with short single-shot k-space trajectories. The typical duration of readouts varies from 10 ms to 20 ms and such long readouts cause severe blurring due to concomitant fields at low field. The MaxGIRF approach can be directly applied to reconstruct MRF images in a frame-by-frame manner and mitigate blurring caused by concomitant fields particularly in FISP-based MRF. The MaxGIRF could be combined with a low-rank and subspace modeling approach with and without a sparsity term along temporal dimension.

Turning now to FIG. 1, an example embodiment of a MRI reconstruction system may include a computing system 100. The computing system 100 may include a computing apparatus 102. The computing apparatus 102 may include one or more processors 104, a memory 106 and/or a bus 112 and/or other mechanisms for communicating between the one or more processors 104. The one or more processors 104 may be implemented as a single processor or as multiple processors. The one or more processors 104 may execute instructions stored in the memory 106 to implement the applications and/or detection of the computing system 100.

The one or more processors 104 may be coupled to the memory 106. The memory 106 may include one or more of a Random Access Memory (RAM) or other volatile or non-volatile memory. The memory 106 may be a non-transitory memory or a data storage device, such as a hard disk drive, a solid-state disk drive, a hybrid disk drive, or other appropriate data storage, and may further store machine-readable instructions, which may be loaded and executed by the one or more processors 104.

The memory 106 may include one or more of random access memory ("RAM"), static memory, cache, flash memory and any other suitable type of storage device or computer readable storage medium, which is used for storing instructions to be executed by the one or more processors 104. The storage device or the computer readable storage medium may be a read only memory ("ROM"), flash memory, and/or memory card, that may be coupled to a bus 112 or other communication mechanism. The storage device may be a mass storage device, such as a magnetic disk, optical disk, and/or flash disk that may be directly or indirectly, temporarily or semi-permanently coupled to the bus 112 or other communication mechanism and be electrically coupled to some or all of the other components within the computing system 100 including the memory 106, the user interface 110 and/or the communication interface 108 via the bus 112.

The term "computer-readable medium" is used to define any medium that can store and provide instructions and other data to a processor, particularly where the instructions are to be executed by a processor and/or other peripheral of the processing system. Such medium can include non-volatile storage, volatile storage and transmission media. Non-volatile storage may be embodied on media such as optical or magnetic disks. Storage may be provided locally and in physical proximity to a processor or remotely, typically by use of network connection. Non-volatile storage may be removable from computing system, as in storage or memory cards or sticks that can be easily connected or disconnected from a computer using a standard interface.

The system 100 may include a user interface 110. The user interface 110 may include an input/output device. The input/output device may receive user input, such as a user interface element, hand-held controller that provides tactile/proprioceptive feedback, a button, a dial, a microphone, a keyboard, or a touch screen, and/or provides output, such as a display, a speaker, an audio and/or visual indicator, or a refreshable braille display. The display may be a computer display, a tablet display, a mobile phone display, an augmented reality display or a virtual reality headset. The display may output or provide a virtual environment that mimics actions of the patient and/or provide information regarding the neural activity of the patient or other information.

The user interface 110 may include an input/output device that receives user input, such as a user interface element, a button, a dial, a microphone, a keyboard, or a touch screen, and/or provides output, such as a display, a speaker, headphones, an audio and/or visual indicator, a device that provides tactile/proprioceptive feedback or a refreshable braille display. The speaker may be used to output audio. The user interface 110 may receive user input that may include configuration settings for one or more user preferences, such as a selection, for example.

The system 100 may have a network 116 that connects to a server 114. The network 116 may be a local area network (LAN), a wide area network (WAN), a cellular network, the Internet, or combination thereof, that connects, couples and/or otherwise communicates between the various components of the system 100 with the server 114. The server 114 may be a remote computing device or system that includes a memory, a processor and/or a network access device coupled together via a bus. The server 114 may be a computer in a network that is used to provide services, such as accessing files or sharing peripherals, to other computers in the network.

The system 100 may include a communication interface 108, such as a network access device. The communication interface 108 may include a communication port or channel, such as one or more of a Dedicated Short-Range Communication (DSRC) unit, a Wi-Fi unit, a Bluetooth® unit, a radio frequency identification (RFID) tag or reader, or a cellular network unit for accessing a cellular network (such as 3G, 4G, or 5G). The communication interface may transmit data to and receive data among the different components.

The server 114 may include a database. A database is any collection of pieces of information that is organized for search and retrieval, such as by a computer, and the database may be organized in tables, schemas, queries, reports, or any other data structures. A database may use any number of database management systems. The information may include real-time information, periodically updated information, or user-inputted information. The various types or kinds of servers 114 that are part of the MRI reconstruction system are further described below.

With reference to FIGS. 1 and 2, the MRI reconstruction system may include an MRI system 200. The MRI system 200 may include the computing system 100, as described above including the computing apparatus 102, the one or more servers 114 and/or the user interface 110. The one or more servers 114 may include a data store server, a pulse sequence server, a data acquisition server, a data processing server or another type or kind of server. The computing apparatus 102 may be coupled and connected to the one or more servers 114, such as via a network 116, as described above.

The MRI system 200 may include other components including a gradient system 202, a physiological acquisition controller 204, a scan room interface 206, a patient positioning system 210, an radiofrequency (RF) system 208, a gradient coil assembly 212. The gradient system 202 may excite the gradient coils in the gradient coil assembly 212. The gradient coils in the gradient coil assembly 212 produce the magnetic field gradients that are used to encode the magnetic resonance signals. The magnetic assembly 216 may include a polarizing magnet 214 and an RF coil 218.

The RF system 208 may be coupled to the RF coil 218 and may provide RF waveforms to the RF coil 218 to be applied on the patient to perform magnetic resonance imaging. The RF coil 218 may detect magnetic resonance signals. The RF system 208 may amplify, demodulate, filter and digitize the magnetic resonance signals. The RF system 208 may include an RF transmitter. The RF system 208 may store the magnetic resonance signals in the data acquisition server. The data acquisition server may receive the magnetic resonance signals and provide storage for the magnetic resonance signals. The data acquisition server may acquire the magnetic resonance signals and process the magnetic resonance signals in real-time to produce derived information that is used to control the scan, such as derived information that may be provided to the pulse sequence server to calibrate the pulse sequence server to emit or provide pulse sequences.

The data processing server may receive the magnetic resonance data from the data acquisition server and may reconstruct a two-dimensional (2D) or a three-dimensional (3D) image of the magnetic resonance data. The data processing server may reconstruct the 2D or 3D image from the magnetic resonance data, such as by performing a Fourier transformation of the k-space data to reconstruct the 2D or 3D image. The data processing server may provide the reconstructed 2D or 3D image to be displayed on the user interface 118 of the computing system 100.

The pulse sequence server may control the RF system 208 and/or the RF transmitter of the RF system 208 to produce RF pulses at a desired frequency, phase, and amplitude, which may be emitted through the RF coil 208 to be applied on the patient. The pulse sequence server may receive patient data from the physiological acquisition controller 204. The physiological acquisition controller 204 may be coupled to one or more sensors that measure or detect physiological parameters of the patient. The one or more sensors may include an electrocardiograph or a respiratory monitoring device to measure a respiratory signal. The physiological acquisition controller 204 may be coupled to the pulse sequence server and synchronize the scan of the patient with the parameter of the patient, such as the heartbeat or respiration of the patient.

The pulse sequence server may be coupled to a scan room interface 206. The scan room interface 206 may receive sensor data related to a condition of the patient and/or may provide commands through to other components, such as the patient positioning system 210. The patient positioning system 210 may receive commands to move the patient to a desired position during the scan.

FIG. 3 is a flow diagram of a process 300 for reconstructing and providing an MRI image to a clinician or other user or health professional. Referring to FIGS. 1, 2, and 3, one or more computers or one or more data processing apparatuses, for example, the processor 104 (FIG. 1) of the computing system 100 (FIG. 1) of the MRI reconstruction system, appropriately programmed, may implement the process 300.

The MRI reconstruction system may include an MRI scanner 202. The MRI scanner 202 may obtain MRI data, such as image data or k-space data (block 302). The MRI scanner 202 may obtain the image data or the k-space data of a portion of a patient, such as a human patient. The image data or the k-space data may be representative of the portion of the patient and be transformed to form a reconstructed MRI image that has less blurring and/or artifacts.

The MRI reconstruction system maps the location of voxels of the image data or the k-space data in the reference coordinate system (RCS) to spatial coordinates in the physical coordinate system (PCS) (block 304). The voxels in the image data or the k-space data may be described by its row, column, and slice position within the RCS. The MRI reconstruction system uses a right-handed Cartesian coordinate system that has an origin as its isocenter. This right-handed Cartesian coordinate system may be referred to as the PCS. Thus, the MRI reconstruction system determines the position of the voxel that is initially in the RCS in terms of the PCS to provide as input into the analytic concomitant field model.

The MRI reconstruction system converts or calculates the locations of the voxels of the image data or the k-space data, which may be represented in a matrix or reference coordinate system (RCS) into spatial coordinates for the image data or k-space data that may be represented in a physical coordinate system (PCS). The MRI reconstruction system performs one or more translations and/or rotations to transition, calculate or otherwise change the locations of the voxels of the image data or the k-space data represented in the RCS to the PCS. The MRI reconstruction system may transform the location of the voxel in a matrix or RCS to spatial coordinate of the voxel in the PCS via one or more intermediate coordinate systems, such as the logical coordinate system (LCS) and/or a patient coordinate system (PAT), and then to PCS. For example, the MRI reconstruction system may transform the location of the voxel from RCS to LCS, from LCS to PAT, and finally from PAT to PCS by applying rotation and translation of the voxels matrix coordinates in a matrix or RCS.

The MRI reconstruction system may obtain a nominal or desired gradient waveforms (block 306). Once the MRI reconstruction system has obtained the nominal or desired gradient waveforms, the MRI reconstruction system may determine the actual gradient waveforms (block 308). The MRI reconstruction system may apply a convolution to the nominal gradient waveforms to determine the actual gradient waveforms. The MRI reconstruction system may apply the convolution to the nominal gradient waveforms to obtain an input, such as the actual gradient waveforms, that is provided into the analytic concomitant field model to reconstruct the MRI image. The convolution may be applied using a gradient impulse response function (GIRF) to determine predicted or distorted gradient waveforms. The predicted or distorted gradient waveforms may be produced by gradient coils of the MRI scanner.

The MRI reconstruction system 100 generates a forward model (block 310). The MRI reconstruction system determines or identifies terms of the image data or k-space data. The model identifies the high-order concomitant field terms along with linear Fourier terms of the image data or the k-space data that are to be used to reconstruct the MRI image more accurately than without the high-order concomitant field terms. The high-order concomitant field terms may cause a reduction in local blurring of the MRI image and may correct or reduce artifacts in the MRI image to reduce distortion or disturbance in the reconstructed MRI image.

The MRI reconstruction system reconstructs the MRI image (block 312). The MRI reconstruction system uses an analytic concomitant field model that incorporates the high-order concomitant field terms and that is computed with distorted gradient waveforms and voxels' physical coordinates to the k-space data to reconstruct the MRI image. The MRI reconstruction system reconstructs the MRI image based on the coil sensitivities of the MRI scanner, the analytic concomitant field model, and the initially obtained image data and/or k-space data. The reconstruction of the MRI image data results in an image with less distortions and/or disturbances. The MRI image reconstruction system may use a conjugate gradient algorithm or an iterative solver on the image data or the k-space data to recover the MRI image without artifacts. The reconstructed MRI image may be represented by an image vector and/or a matrix that represents the reconstructed MRI image.

The MRI reconstruction system may provide the reconstructed MRI image to a user, such as a clinician, an operator or other health professional (block 314). The MRI reconstruction system may render the reconstructed MRI image on a display or other output device.

Having introduced operative principles, various configurations and embodiments, and a method of MRI reconstruction, attention now turns to a combination of FIGS. 1-9 and a discussion of example embodiments of the aforementioned technologies. These different embodiments are discussed briefly below.

For instance, an image reconstruction system may be provided. The system may include a memory and a processor. The memory may be configured to store magnetic resonance imaging (MRI) data. The processor is coupled to the memory and may be configured to reconstruct a magnetic resonance imaging (MRI) image based on the MRI data and using an analytic concomitant field model to reduce distortion or disturbance in the reconstructed MRI image.

The image reconstruction system can include one or more additional aspect as well. For example, the MRI data may be image data. The MRI data may be k-space data. To reconstruct the MRI image based on the MRI data and using the analytic concomitant field model, the processor is configured to use high-order concomitant field terms along with linear Fourier terms of the MRI data to reconstruct the MRI image more accurately than without the high-order concomitant field terms to reconstruct the MRI image. Using the high-order concomitant field terms in the reconstruction of the MRI image causes a reduction in local blurring of the MRI image and corrects or reduces artifacts in the MRI image to reduce distortion or disturbance in the reconstructed MRI image. The analytic concomitant field model identifies, uses and incorporates the high-order concomitant field terms in addition to the linear Fourier terms of the image data or the k-space data to reconstruct the MRI image. The processor may be configured to reconstruct the MRI image further based on one or more receiver coil sensitivities of a MRI scanner that may be used to capture the MRI data. To reconstruct the magnetic resonance imaging (MRI) image based on the MRI data and using the analytic concomitant field model, the processor may be configured to calculate or determine an image vector or matrix that represents the reconstructed MRI image using a conjugate gradient algorithm or an iterative solver on the MRI data to recover the MRI image without artifacts.

The system may include an MRI scanner configured to obtain the MRI data of a patient. The processor may be configured to calculate spatial coordinates of a voxel of the MRI data in a physical coordinate system (PCS) including translating or rotating a location of the voxel in a reference coordinate system (RCS) to the PCS. The processor may be configured to apply a convolution of inputted nominal gradient waveforms or field with a gradient impulse response function (GIRF) to determine predicted or distorted gradient waveforms produced by gradient coils of the MRI scanner. The processor may be configured to apply the analytic concomitant field model computed with distorted gradient waveforms and voxels' physical coordinates to the MRI data.

The system may also include a display configured to output the reconstructed MRI image to a user. The processor may be configured to output, provide or render on the display the reconstructed MRI image to the user.

A method for reconstructing a magnetic resonance imaging (MRI) image is provided. The method may include obtaining, by a processor, MRI data of a patient. The method may include determining, by the processor, spatial coordinates of voxels of the MRI data in a physical coordinate system (PCS). The method may include applying a convolution of inputted nominal gradient waveforms with a gradient impulse response function (GIRF) to determine predicted or distorted gradient waveforms. The method may include applying the analytic concomitant field model computed with distorted gradient waveforms and voxels' physical coordinates to the MRI data. The method may include providing, by the processor, the MRI image to a user.

Various embodiments include one or more additional aspect as well. For example, the MRI data may be image data. The MRI data may be k-space data. Determining the spatial coordinates of the voxels of the MRI data in the PCS may include translating or rotating location of voxels in RCS to the PCS. The analytic concomitant field model may identify, use and incorporate high-order concomitant field terms in addition to linear Fourier terms of the MRI data to reconstruct the MRI image. Reconstructing the MRI image may be further based on one or more receiver coil sensitivities of a MRI scanner that used to capture the MRI data.

A non-transitory computer-readable medium is provided. The medium may include computer readable instructions, which when executed by a processor, cause the processor to perform operations. The operations may include obtaining image data or k-space data of a patient and calculating spatial coordinates of voxels in a physical coordinate system (PCS). The operations may include applying a convolution of inputted nominal gradient field waveforms with a gradient impulse response function (GIRF) to determine predicted or distorted gradient waveforms and applying the analytic concomitant field model computed with distorted gradient waveforms and voxels' physical coordinates to the image data or the k-space data. The operations may include providing a MRI image to a user.

Various embodiments include one or more additional aspect as well. To calculate the spatial coordinates of the voxels in the PCS the operations may include rotating or translating a location of the voxels in a matrix or reference coordinate system (RCS) to the PCS. In various embodiments, the analytic concomitant field model identifies, uses and incorporates high-order concomitant field terms in addition to linear Fourier terms of the image data or the k-space data to reconstruct the MRI image.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

In various embodiments, software may be stored in a computer program product and loaded into a computer system using a removable storage drive, hard disk drive, or communications interface. The control logic (software), when executed by the processor, causes the processor to perform the functions of various embodiments as described herein. In various embodiments, hardware components may take the form of application specific integrated circuits (ASICs). Implementation of the hardware so as to perform the functions described herein will be apparent to persons skilled in the relevant art(s).

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an Internet-based embodiment, an entirely hardware embodiment, or an embodiment combining aspects of the Internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, BLU-RAY DISC®, optical storage devices, magnetic storage devices, and/or the like.

What is claimed is:

1. An image reconstruction system, comprising:

a magnetic resonance imaging (MRI) system having symmetric x and y gradient coils and configured to capture or obtain MRI data including k-space data of a patient;

a memory configured to store the MRI data; and a processor coupled to the MRI system and the memory and configured to:

receive the k-space data from the MRI system or the memory;

apply a convolution of inputted nominal gradient waveforms with gradient impulse response functions (GIRFs) to determine predicted or distorted gradient waveforms produced by the symmetric x and y gradient coils of the MRI system;

calculate or determine linear Fourier terms of the k-space data and concomitant field terms arising from the predicted or distorted gradient waveforms without imposing approximations on k-space trajectories when calculating or determining the concomitant field terms;

calculate or determine an image vector or matrix by solving a cost function that describes the relationship between the captured or obtained k-space data and an image using a conjugate gradient algorithm or an iterative solver and a nonuniform fast Fourier transform (NUFFT) for the linear Fourier terms; and reconstruct an MRI image using the approximation-free concomitant field terms, the predicted or distorted gradient waveforms calculated with GIRFs, a measured field map or a static off-resonance map, and the image vector or matrix.

2. The image construction system of claim 1, wherein the image is further calculated or determined using an approximation on an encoding operator that allows for the use of a nonuniform fast Fourier transform (NUFFT).

3. The image reconstruction system of claim 1, wherein using the concomitant field terms in the reconstruction of the MRI image causes a reduction in local blurring of the MRI image and corrects or reduces artifacts in the MRI image to reduce distortion or disturbance in the reconstructed MRI image.

4. The image reconstruction system of claim 1, wherein the MRI system includes an MRI scanner configured to obtain the MRI data of the patient; and wherein the processor is configured to:

calculate spatial coordinates of a voxel of the MRI data in a physical coordinate system (PCS) including translating or rotating a location of the voxel in a reference coordinate system (RCS) to the PCS.

5. The image reconstruction system of claim 1, further comprising:

a display configured to output the reconstructed MRI image to a user;

wherein the processor is configured to:

output, provide or render on the display the reconstructed MRI image to the user.

6. A method for reconstructing a magnetic resonance imaging (MRI) image using an MRI system having symmetric x and y gradient coils, the method comprising:

obtaining, by the MRI system, MRI data including k-space data of a patient;

applying a convolution of inputted nominal gradient waveforms with a gradient impulse response function (GIRF) to determine predicted or distorted gradient waveforms produced by the symmetric x and y gradient coils of the MRI system, wherein GIRF measurements are acquired without using a field monitoring device, a field camera or field probes;

calculating or determining, by the MRI system, linear Fourier terms of the k-space data and concomitant field terms arising from the predicted or distorted gradient waveforms without imposing approximations on k-space trajectories when calculating or determining concomitant field terms;

calculating or determining, by the MRI system, an image vector or matrix by solving a cost function that describes the relationship between the captured or obtained k-space data and an image using a conjugate gradient algorithm or an iterative solver and a computational routine for the linear Fourier terms; and reconstructing, by the MRI system, an MRI image using the approximation-free concomitant field terms, the predicted or distorted gradient waveforms calculated with GIRFs, a measured field map or a static off-resonance map, and the image vector or matrix;

and providing, by the MRI system, the reconstructed MRI image to a user.

7. The method of claim 6, wherein the computational routine includes using a low-rank approximation on an encoding operator that allows for the use of a nonuniform fast Fourier transform (NUFFT).

8. The method of claim 6, wherein reconstructing the MRI image is further based on one or more receiver coil sensitivities of the MRI system used to capture the MRI data.

* * * * *